US012762699B2

(12) United States Patent
Horiuchi et al.

(10) Patent No.: US 12,762,699 B2
(45) Date of Patent: Oct. 13, 2026

(54) INFORMATION PROCESSING APPARATUS, INFORMATION PROCESSING METHOD, AND INFORMATION PROCESSING PROGRAM

(71) Applicant: FUJIFILM Corporation, Tokyo (JP)

(72) Inventors: Hisatsugu Horiuchi, Kanagawa (JP); Seiki Morita, Kanagawa (JP); Takashi Mizoguchi, Kanagawa (JP); Sachie Wada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 249 days.

(21) Appl. No.: 18/596,577

(22) Filed: Mar. 5, 2024

(65) Prior Publication Data

US 2024/0303810 A1 Sep. 12, 2024

(30) Foreign Application Priority Data

Mar. 10, 2023 (JP) ................................ 2023-038160

(51) Int. Cl.

| | |
|---|---|
| ***G06T 7/00*** | (2017.01) |
| ***G06T 3/40*** | (2006.01) |
| ***G06V 10/44*** | (2022.01) |
| ***G16H 30/40*** | (2018.01) |

(52) U.S. Cl.

CPC .............. *G06T 7/0012* (2013.01); *G06T 3/40* (2013.01); *G06V 10/44* (2022.01); *G16H 30/40* (2018.01); *G06T 2207/10081* (2013.01); *G06T 2207/10088* (2013.01); *G06T 2207/10132* (2013.01);

(Continued)

(58) Field of Classification Search

CPC ............. G06V 10/44; G06T 3/40; G06T 7/33; G06T 7/0012; G06T 2207/10081; G06T 2207/20044; G06T 2207/10088; G06T 2207/30068; G06T 2207/10132; G16H 30/40; G16H 30/20; A61B 6/5235;

(Continued)

(56) References Cited

U.S. PATENT DOCUMENTS

2007/0003118 A1* 1/2007 Wheeler .................. G06T 7/38 382/128
2012/0114213 A1* 5/2012 Buelow .................. G06T 7/344 382/131
2017/0064208 A1* 3/2017 Salimpour ........... G06F 3/0484

(Continued)

FOREIGN PATENT DOCUMENTS

JP 2004283366 A * 10/2004
JP 2017-176509 A 10/2017
WO WO-2021051128 A1 * 3/2021 .......... A61B 8/4263

*Primary Examiner* — Tracy Mangialaschi
(74) *Attorney, Agent, or Firm* — Studebaker Brackett PLLC

(57) ABSTRACT

An information processing apparatus including at least one processor, wherein the processor is configured to: acquire a first medical image of an examinee associated with a first reference position specified based on a physical feature of the examinee included in a first optical image obtained by optically imaging the examinee; acquire a second medical image of the examinee associated with the first reference position or a second reference position indicating a position substantially the same as the first reference position; and output a result of associating the first medical image with the second medical image based on the first reference position and the second reference position.

20 Claims, 14 Drawing Sheets

(52) U.S. Cl.
CPC ............... *G06T 2207/20044* (2013.01); *G06T 2207/30068* (2013.01)

(58) Field of Classification Search
CPC ..... A61B 6/5247; A61B 6/5241; A61B 6/502; A61B 6/5264
See application file for complete search history.

(56) References Cited

U.S. PATENT DOCUMENTS

| | | | | |
|---|---|---|---|---|
| 2017/0281131 | A1 | 10/2017 | Sendai | |
| 2021/0183150 | A1* | 6/2021 | Walle-Jensen | G06T 19/006 |

* cited by examiner

INFORMATION PROCESSING APPARATUS, INFORMATION PROCESSING METHOD, AND INFORMATION PROCESSING PROGRAM

CROSS-REFERENCE TO RELATED APPLICATIONS

This application claims priority from Japanese Application No. 2023-038160, filed on Mar. 10, 2023, the entire disclosure of which is incorporated herein by reference.

BACKGROUND

Technical Field

The present disclosure relates to an information processing apparatus, an information processing method, and an information processing program.

Related Art

In the related art, a mammography apparatus that captures a radiation image of a breast is known. In addition, in the terms of improving the detection accuracy of a lesion and improving the efficiency of an examination, an apparatus that can capture an ultrasound image of a breast in addition to a radiation image is proposed. For example, JP2017-176509A discloses an apparatus that captures a radiation image and an ultrasound image of a breast put into a compressed state by a compression member.

In addition, for example, JP2004-283366A discloses that a radiation image and an optical image of an examinee are acquired, a misregistration amount between a newly acquired optical image and a past optical image is calculated in a case in which the radiation image is newly acquired, and whether or not the misregistration amount is equal to or smaller than a reference value. In the technique described in JP2004-283366A, a marker is given to the examinee such that the marker is imaged in the optical image, so that a misregistration amount based on the marker is calculated.

In recent years, there are an increasing opportunity to perform the comparative image interpretation by imaging one subject a plurality of times. In addition, for example, there are an increasing opportunity to perform the comparative image interpretation by combining a plurality of different types of medical images of mammography, ultrasound imaging, computed tomography (CT), magnetic resonance imaging (MRI), and the like. Along with this, there is an increasing demand for facilitating the comparative image interpretation by performing the registration between the plurality of medical images. In the technique described in JP2004-283366A, the marker is used to calculate the misregistration amount, and it takes time and effort to mount the marker. In particular, in the mammography, there is a case in which the imaging is performed with an upper body exposed, and it is desired to perform registration without using such a marker.

SUMMARY

The present disclosure provides an information processing apparatus, an information processing method, and an information processing program that can perform registration for a plurality of medical images related to the same subject even in a case in which subject portions do not completely match each other or states of the subject portions do not completely match each other.

A first aspect of the present disclosure relates to an information processing apparatus comprising: at least one processor, in which the processor acquires a first medical image of an examinee associated with a first reference position specified based on a physical feature of the examinee included in a first optical image obtained by optically imaging the examinee, acquires a second medical image of the examinee associated with the first reference position or a second reference position indicating a position substantially the same as the first reference position, and outputs a result of associating the first medical image with the second medical image based on the first reference position and the second reference position.

In the first aspect, the processor may acquire the first optical image, may specify the first reference position based on the physical feature of the examinee included in the first optical image, and may associate the first medical image with the specified first reference position.

In the first aspect, the first optical image and the first medical image may be images captured at first points in time that are substantially the same each other.

In the first aspect, the processor may acquire a second optical image obtained by optically imaging the examinee at a second point in time that is substantially the same as an imaging point in time of the second medical image, may specify the second reference position based on a physical feature of the examinee included in the second optical image, and may associate the specified second reference position with the second medical image.

In the first aspect, the processor may store the result of associating the first medical image with the second medical image in a storage unit.

In the first aspect, the processor may perform registration between the first medical image and the second medical image based on the first reference position and the second reference position, to display the first medical image and the second medical image on a display or to print the first medical image and the second medical image on paper by using a printer.

In the first aspect, the first optical image may be an image obtained by optically imaging a portion that is not included in the first medical image of the examinee.

In the first aspect, the physical feature of the examinee may be a joint point of the examinee.

In the first aspect, the first optical image may be an image obtained by imaging the examinee from a back surface side of the examinee.

In the first aspect, the first optical image may be an image obtained by imaging the examinee from an upper side of a head of the examinee.

In the first aspect, the first optical image may be at least one of a visible light image or a depth image.

In the first aspect, the first medical image may be a mammography image, and the second medical image may be an ultrasound image.

In the first aspect, the first medical image may be a mammography image, and the second medical image may be a computed tomography image.

In the first aspect, the first medical image may be a mammography image, and the second medical image may be a magnetic resonance image.

In the first aspect, the first medical image may be a mammography image of a left breast of the examinee, and the second medical image may be a mammography image of a right breast of the examinee.

In the first aspect, the first medical image may be a mammography image captured by setting an imaging distance from a focus of a radiation source to a breast as a subject to a first distance, the second medical image may be a magnification mammography image captured by setting the imaging distance to a second distance shorter than the first distance, and the processor may derive a magnification ratio of the second medical image based on the second distance, may reduce the second medical image based on the magnification ratio, and may output a result of associating the reduced second medical image with the first medical image.

A second aspect of the present disclosure relates to an information processing method comprising: acquiring a first medical image of an examinee associated with a first reference position specified based on a physical feature of the examinee included in a first optical image obtained by optically imaging the examinee; acquiring a second medical image of the examinee associated with the first reference position or a second reference position indicating a position substantially the same as the first reference position; and outputting a result of associating the first medical image with the second medical image based on the first reference position and the second reference position.

A third aspect of the present disclosure relates to an information processing program for causing a computer to execute a process comprising: acquiring a first medical image of an examinee associated with a first reference position specified based on a physical feature of the examinee included in a first optical image obtained by optically imaging the examinee; acquiring a second medical image of the examinee associated with the first reference position or a second reference position indicating a position substantially the same as the first reference position; and outputting a result of associating the first medical image with the second medical image based on the first reference position and the second reference position.

According to the aspects described above, in the information processing apparatus, the information processing method, and the information processing program according to the present disclosure, it is possible to perform the registration for the plurality of medical images related to the same subject even in a case in which the subject portions do not completely match each other or the states of the subject portions do not completely match each other.

DETAILED DESCRIPTION

Hereinafter, a description of an embodiment of the present disclosure will be made with reference to the accompanying drawings.

Figure 1:
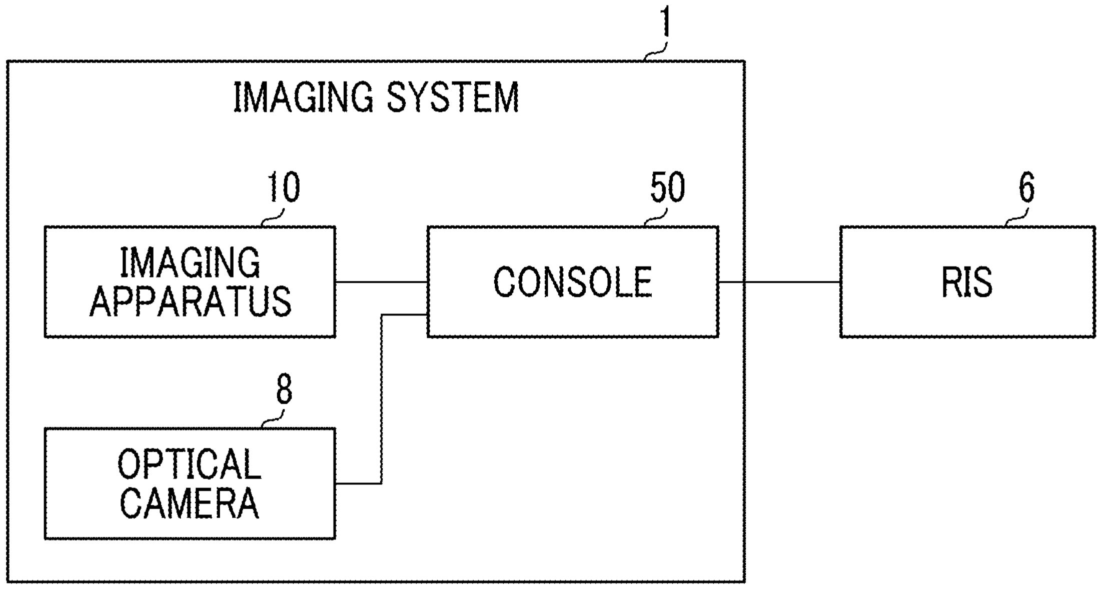
FIG. 1 is a view showing an example of a schematic configuration of an imaging system.

First, a description of a configuration of an imaging system 1 will be made with reference to FIG. 1. FIG. 1 is a view showing an example of a schematic configuration of the imaging system 1. As shown in FIG. 1, the imaging system 1 comprises an imaging apparatus 10, a console 50, and an optical camera 8. The imaging apparatus 10 and the console 50, the optical camera 8 and the console 50, and the console 50 and an external radiology information system (RIS) 6 are configured to be connected to each other via a wired or wireless network.

In the imaging system 1, the console 50 acquires an imaging order or the like from the RIS 6, and controls the imaging apparatus 10 in accordance with the imaging order, an instruction from the user, and the like. The imaging apparatus 10 acquires a radiation image and an ultrasound image of a breast of an examinee put into a compressed state by a compression member 40 as a subject. The console 50 is an example of an information processing apparatus according to the present disclosure.

Figure 2:
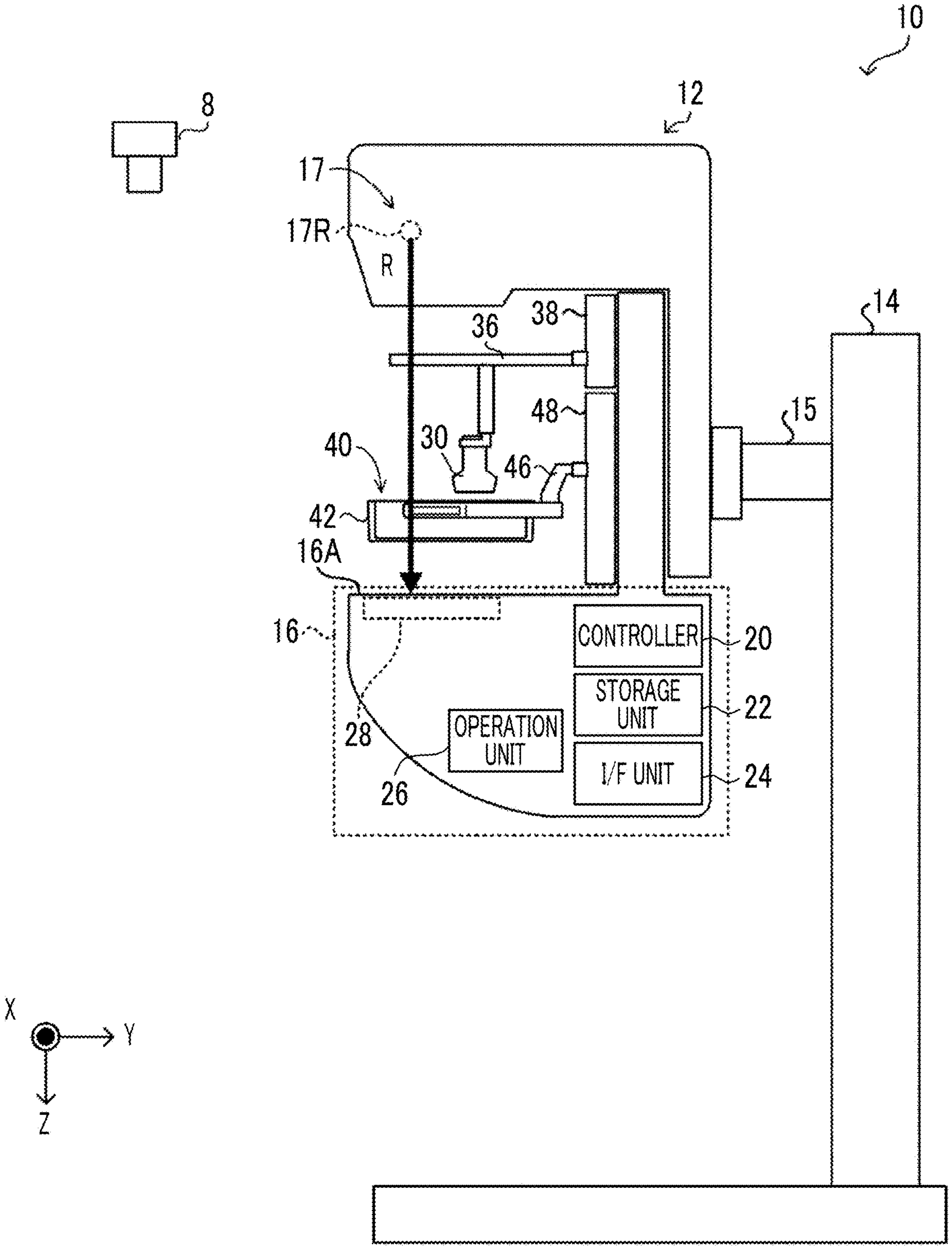
FIG. 2 is a side view showing an example of an appearance of an imaging apparatus.

Next, a description of a schematic configuration of the imaging apparatus 10 will be made with reference to FIG. 2. FIG. 2 is a side view showing an example of an appearance of the imaging apparatus 10, and is a view in a case in which the imaging apparatus 10 is viewed from a right side of the examinee. As shown in FIG. 2, the imaging apparatus 10 comprises a radiation source 17R, a radiation detector 28, an imaging table 16 disposed between the radiation source 17R and the radiation detector 28, the compression member 40 that compresses a breast 2 between the compression member 40 and the imaging table 16, and an ultrasound probe 30 disposed between the radiation source 17R and the compression member 40. In the imaging apparatus 10, a user, such as a doctor or a technician, positions the breast 2 of the examinee on an imaging surface 16A of the imaging table 16.

The imaging apparatus 10 comprises an arm part 12, a base 14, and a shaft part 15. The arm part 12 is held to be movable in an up-down direction (Z direction) by the base 14. The shaft part 15 connects the arm part 12 to the base 14. The arm part 12 is relatively rotatable with respect to the base 14 with the shaft part 15 as a rotation axis. In addition, the arm part 12 may be relatively rotatable with respect to the base 14 with the shaft part 15 as the rotation axis separately between an upper part comprising a radiation emitting unit 17 and a lower part comprising the imaging table 16.

The arm part 12 comprises the radiation emitting unit 17 and the imaging table 16. The radiation emitting unit 17 comprises the radiation source 17R, and is configured to change an irradiation field of radiation (for example, X-rays) emitted from the radiation source 17R. For example, the change of the irradiation field may be performed by the user operating an operation unit 26, or may be performed by a controller 20 in accordance with a type of the attached compression member 40. The radiation source 17R irradiates the breast put into the compressed state by the compression member 40 with radiation R.

The imaging table 16 comprises the controller 20, a storage unit 22, an interface (I/F) unit 24, the operation unit 26, and the radiation detector 28. The controller 20 controls an overall operation of the imaging apparatus 10 in accordance with the control of the console 50. The controller 20 comprises a central processing unit (CPU), a read only memory (ROM), a random access memory (RAM), and the like (none shown). The ROM stores in advance various programs including a program executed by the CPU for performing the control related to the acquisition of the radiation image and the ultrasound image. The RAM transitorily stores various data.

Data of the radiation image and the ultrasound image, various types of other information, and the like are stored in the storage unit 22. The storage unit 22 is realized by, for example, a storage medium, such as a hard disk drive (HDD), a solid state drive (SSD), and a flash memory.

The I/F unit 24 performs communication of various types of information with the console 50 by wired or wireless communication. Specifically, the I/F unit 24 receives information related to the control of the imaging apparatus 10 from the console 50. Further, the I/F unit 24 transmits the data of the radiation image and the ultrasound image to the console 50.

The operation unit 26 is a part that is provided on the imaging table 16 or the like and can be operated by the user with a hand, a foot, or the like, and is, for example, a switch, a button, or a touch panel. For example, the operation unit 26 may receive a voice input from the user.

The radiation detector 28 is disposed in the imaging table 16, detects the radiation R transmitted through the breast and the imaging table 16, generates the radiation image based on the detected radiation R, and outputs image data indicating the generated radiation image. It should be noted that a type of the radiation detector 28 is not particularly limited and may be, for example, an indirect conversion type radiation detector that converts the radiation R into light and converts the converted light into a charge, or a direct conversion type radiation detector that directly converts the radiation R into a charge.

A probe unit 38 and a compression unit 48 are connected to the arm part 12. A support part 36 that attachably and detachably supports the ultrasound probe 30 is attached to the probe unit 38. The support part 36 (ultrasound probe 30) is moved in the up-down direction (Z direction) and a horizontal direction (X direction and Y direction) by a driving unit (not shown) provided in the probe unit 38. In addition, the support part 36 may be relatively rotatable with respect to the base 14 with an engaging part with the probe unit 38 as a rotation axis. It is preferable that the support part 36 is formed of a material that transmits the radiation R. In addition, it is preferable that the support part 36 is configured to transitorily fix the position of the ultrasound probe 30.

The ultrasound probe 30 is used to obtain the ultrasound image of the breast put into the compressed state by the compression member 40, is disposed between the radiation source 17R and the compression member 40, irradiates the breast with ultrasound via the compression member 40, and receives the reflected waves from the breast. Specifically, the ultrasound probe 30 comprises an ultrasound transducer array. The ultrasound transducer array is configured such that a plurality of ultrasound transducers are arranged one-dimensionally or two-dimensionally. The ultrasound transducer is formed, for example, such that electrodes are formed on both ends of a piezoelectric body, such as a piezoelectric ceramic represented by lead (Pb) zirconate titanate (PZT) or a polymer piezoelectric element represented by polyvinylidene difluoride (PVDF). The probe unit 38 includes a converter (not shown) that converts the reflected waves from the breast received by the ultrasound probe 30 into the ultrasound image, and the ultrasound image is obtained by the converter.

In addition, a plurality of types of the ultrasound probes 30 different from each other may be attachable to the imaging apparatus 10. For example, depending on a physique of the examinee (for example, a size of the breast), a tissue composition of the breast (for example, a fat mass and a mammary gland mass), a type of imaging (for example, magnification imaging and spot imaging), and the like, the ultrasound probes 30 having different types from each other may be prepared and can be attached to and detached from the imaging apparatus 10. For example, the ultrasound probes 30 having different performances and dimensions from each other may be selectively used, such as a linear probe having a center frequency of about 7.5 MHz (for superficial use or the like), a convex probe having a center frequency of about 3.5 MHz (for abdomen or the like), and a sector probe having a center frequency of about 2.5 MHZ (for heart or the like).

A support part 46 that supports the compression member 40 is attachably and detachably attached to the compression unit 48. The support part 46 (compression member 40) is moved in the up-down direction (Z direction) by a driving unit (not shown) provided in the compression unit 48. In addition, the support part 46 may be relatively rotatable with respect to the base 14 with an engaging part with the compression unit 48 as a rotation axis.

Figure 3:
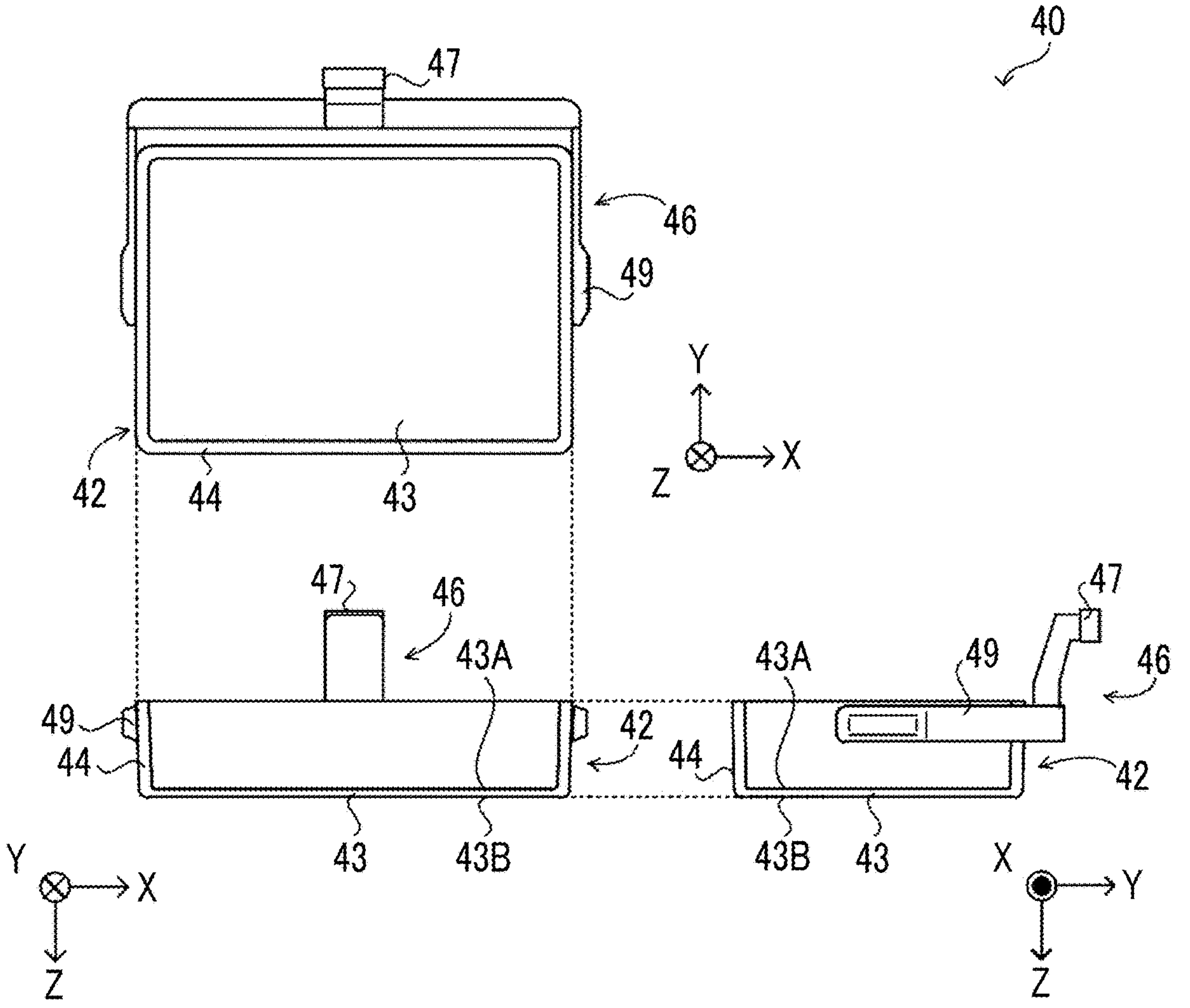
FIG. 3 is a three-orthographic view showing an example of a schematic configuration of a compression member.

The compression member 40 is used to put the breast disposed on the imaging surface 16A into the compressed state. Specifically, the compression member 40 is disposed between the radiation source 17R and the imaging table 16 and interposes the breast between the compression member 40 and the imaging table 16 to put the breast into the compressed state. FIG. 3 shows a three-orthographic view of an example of the compression member 40. The three-orthographic view of FIG. 3 includes a top view of the compression member 40 as viewed from above (radiation emitting unit 17 side), a side view thereof as viewed from the examinee side, and a side view thereof as viewed from the right side of the examinee. As shown in FIG. 3, the compression member 40 includes a compression part 42 and the support part 46.

The support part 46 includes an attachment part 47 and an arm 49. The attachment part 47 attaches the compression member 40 to the imaging apparatus 10, specifically, the driving unit of the compression unit 48. The arm 49 supports the compression part 42.

The compression part 42 includes a bottom part 43 formed to be substantially flat and surrounded by a wall part 44 having a substantially uniform height, and has a cross section shape formed in a recess shape. It is preferable that the compression part 42 is formed of an optically transparent or translucent material in order to perform positioning and check of the compressed state in the compression of the breast. In addition, it is preferable that the compression part 42 is formed of a material excellent in a transmittance of the radiation R and the ultrasound. In addition, it is preferable that the compression part 42 is formed of, for example, a material excellent in strength, such as drop strength and compression strength.

As such a material, for example, resin, such as polymethylpentene (PMP), polycarbonate (PC), acryl, polypropylene (PP), and polyethylene terephthalate (PET), can be used. In particular, in the polymethylpentene, an acoustic impedance, which affects the transmittance and the reflectivity of the ultrasound, is closer to an acoustic impedance of a human body (breast) than other materials, and a proportion of the noise on the ultrasound image can be decreased. Therefore, as the material of the compression part 42, the polymethylpentene is suitable.

In addition, a plurality of types of the compression members 40 different from each other may be attachable to the imaging apparatus 10. For example, depending on a physique of the examinee (for example, a size of the breast), a tissue composition of the breast (for example, a fat mass and a mammary gland mass), a type of imaging (for example, magnification imaging and spot imaging), and the like, compression members 40 having different types from each other may be prepared and can be attached to and detached from the imaging apparatus 10. Specifically, a compression member in accordance with the size of the breast, a compression member for axilla imaging, a compression member for magnification imaging, and a compression member for so-called spot imaging that captures the radiation image of only a region in which a lesion exists, and the like may be used. That is, the compression member 40 is not limited to the compression member that compresses the entire breast, and may have a smaller size than the breast to compress a part of the breast.

Figure 4:
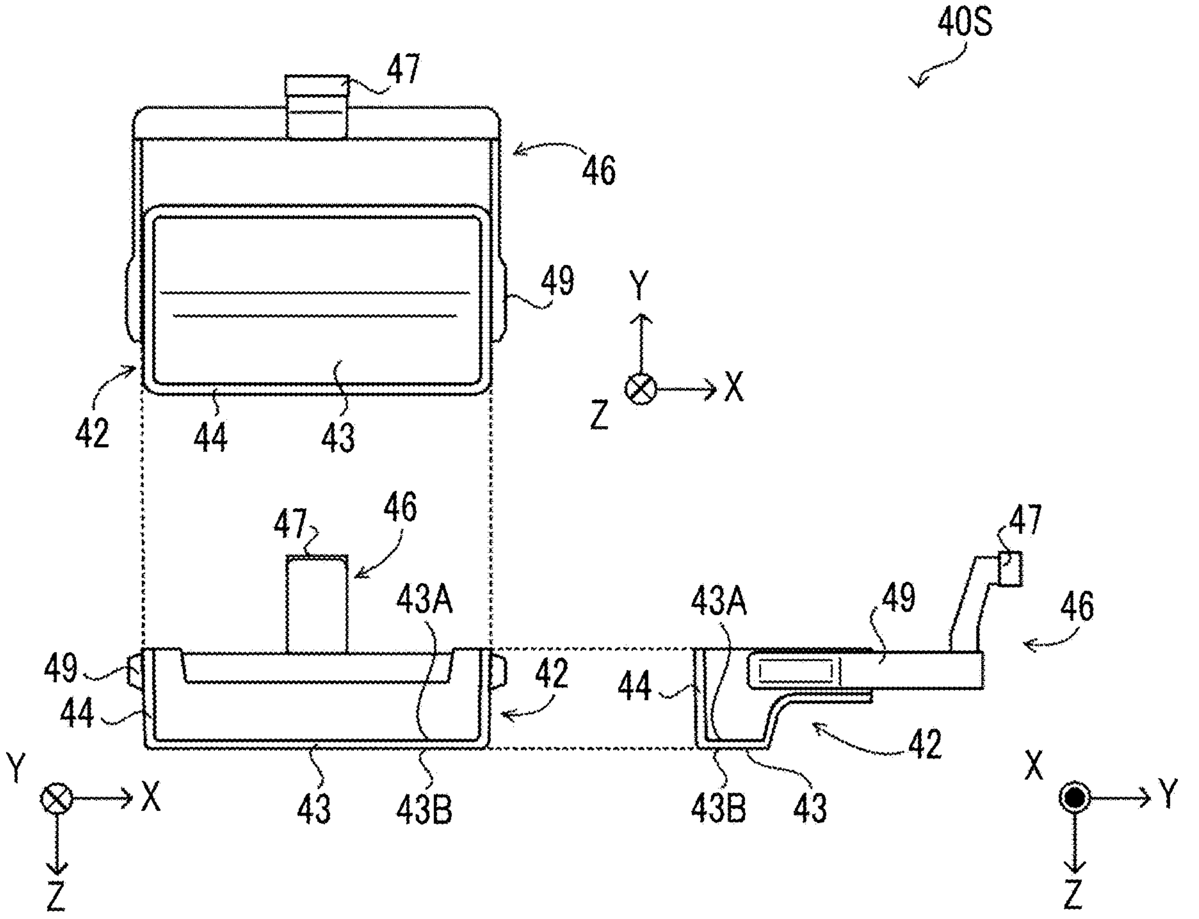
FIG. 4 is a three-orthographic view showing an example of the schematic configuration of the compression member.

FIG. 4 shows a three-orthographic view of a compression member 40S for a small breast as an example of another form different from the compression member 40 of FIG. 3. The three-orthographic view of FIG. 4 includes a top view of the compression member 40S as viewed from above (radiation emitting unit 17 side), a side view thereof as viewed from the examinee side, and a side view thereof as viewed from the right side of the examinee. The compression member 40S includes the compression part 42 and the support part 46, as in the compression member 40 in FIG. 3. In the compression member 40S, the bottom part 43 is not flat, and the attachment part 47 side is higher than a chest wall side (side away from the attachment part 47). In addition, the height of the wall part 44 is not uniform, and a height of a part of the chest wall side is lower than a height of other parts. Due to such a shape, the compression member 40S can easily perform the positioning and the compression even for the small breast.

As described above, in the imaging apparatus 10, at least one of the compression member 40 for putting the breast into the compressed state or the ultrasound probe 30 for acquiring the ultrasound image may be attachable and detachable. That is, a plurality of types of the compression members 40 and the ultrasound probes 30 having different dimensions from each other may be attachable to the imaging apparatus 10. In this case, the imaging apparatus 10 may detect the types of the compression member 40 and the ultrasound probe 30 that are attached.

For example, the attachment part 47 of the compression member 40 may be provided with a plurality of pins having different dispositions for each type of the compression member 40 as identification information, and the identification information may be read by a sensor (for example, a photointerrupter) that can detect the disposition of the pins provided in the compression unit 48. In addition, for example, a marker (for example, a bar code and a two-dimensional code) in accordance with the type of the compression member 40 may be provided at any position of the compression member 40 as identification information, and the identification information may be read by a sensor (for example, a charge coupled device (CCD) sensor) that can detect the marker.

In addition, for example, a radio frequency identification (RFID) tag having identification information in accordance with the type of the compression member 40 may be provided at any position of the compression member 40, and the identification information may be read by an RFID reader that can read the RFID tag. In addition, for example, a weight of each type of the compression member 40 and identification information may be stored in the storage unit 22 in advance in association with each other, the weight of the attached compression member 40 may be measured by a sensor that can detect the weight, and the identification information (type of the compression member 40) may be specified based on a measured value.

Similarly, for the ultrasound probe 30, the type of the attached ultrasound probe 30 may be identified in accordance with, for example, the pin, the marker, the RFID tag, or the weight.

It should be noted that a gel-like or liquid medium having an ultrasound transmittance may be applied to an upper surface 43A of the bottom part 43 of the compression member 40 and/or a contact surface 43B with the breast. As such a medium, for example, a known jelly for an ultrasound examination, which has the acoustic impedance close to the acoustic impedance of the human body (breast), can be applied. That is, the imaging apparatus 10 may acquire the ultrasound image of the breast put into the compressed state by the compression member 40 in a state of being coated with the gel-like or liquid medium having the ultrasound transmittance, via the compression member 40. In this case, it is possible to suppress entry of air into an interface between an ultrasound radiation surface of the ultrasound probe 30 and the upper surface 43A and/or an interface between the contact surface 43B and the breast, and it is possible to reduce a difference in the acoustic impedance at each interface, so that the proportion of the noise applied to the ultrasound image can be decreased.

It should be noted that the method of imaging the breast via the imaging apparatus 10 is not particularly limited. For example, cranio-caudal (CC) imaging, medio-lateral oblique (MLO) imaging, the magnification imaging and the spot imaging for imaging a part of the breast, and the like may be performed. The CC imaging is a method of imaging the breast in the compressed state by interposing the breast between the imaging table 16 and the compression member 40 in the up-down direction (Z direction). The MLO imaging is a method of imaging the breast in the compressed state including an axilla portion by interposing the breast between the imaging table 16 and the compression member 40 in a tilted state in which a rotation angle of the arm part 12 with respect to the base 14 is equal to or greater than 45 degrees and smaller than 90 degrees.

In addition, for example, the imaging apparatus 10 may perform tomosynthesis imaging. In the tomosynthesis imaging, the radiation R is emitted from each of a plurality of irradiation positions having different irradiation angles toward the breast by the radiation source 17R, to capture a plurality of radiation images of the breast. That is, in the tomosynthesis imaging, the imaging is performed by changing the rotation angle of the radiation emitting unit 17 with respect to the base 14 while fixing the angles of the imaging table 16, the compression member 40, the breast, and the like.

In addition, in the imaging apparatus 10, the breast of the examinee may be positioned not only in a state in which the examinee is standing (standing state) but also in a state in which the examinee is sitting on a chair, a wheelchair, or the like (sitting state).

Figure 7:
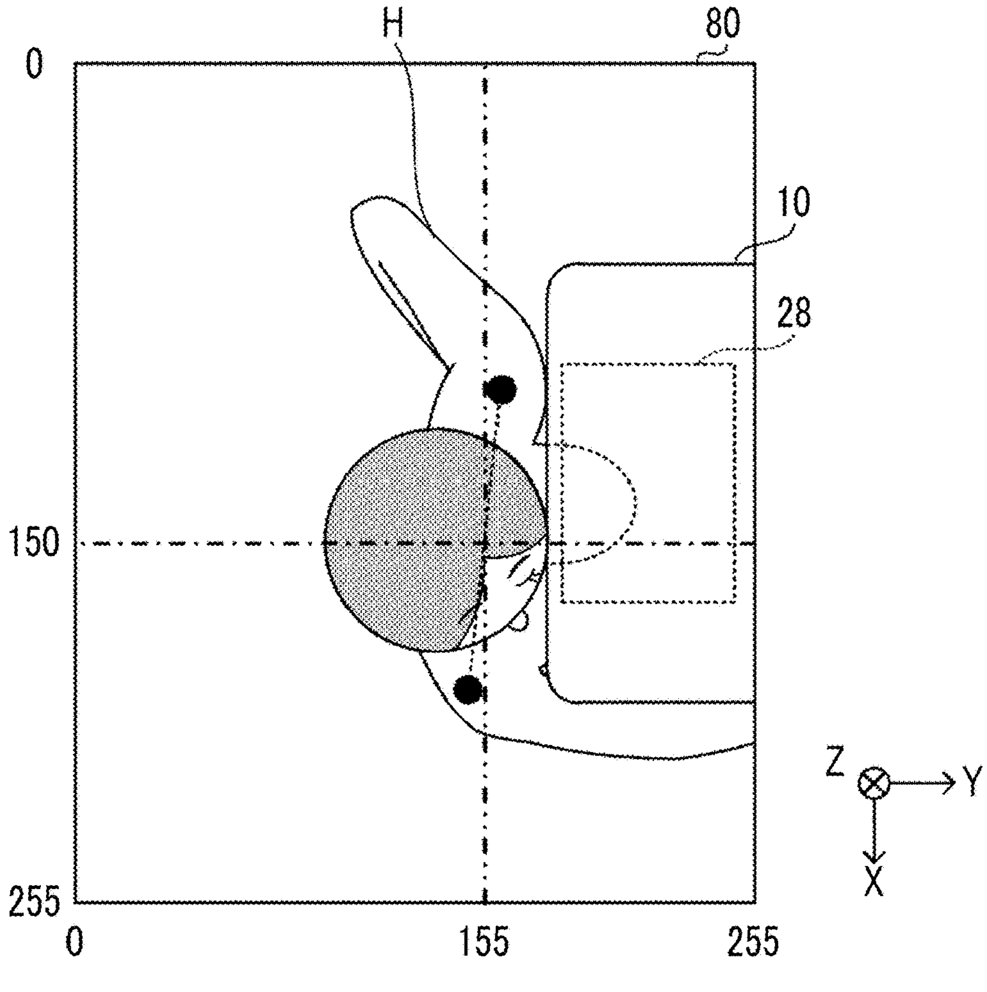
FIG. 7 is a view showing an example of a visible light image.

The optical camera 8 optically images the examinee from an upper side of a head of the examinee to obtain an optical image (see FIG. 7). For example, the optical camera 8 is an optical digital camera that captures a visible light image of the examinee, and includes a complementary metal oxide semiconductor (CMOS) type image sensor or a charge coupled device (CCD) type image sensor. A positional relationship between the optical camera 8 and the imaging apparatus 10 (particularly, the radiation detector 28 or the irradiation field) is determined in advance. It should be noted that the optical camera 8 may be provided, for example, on the arm part 12 or the like of the imaging apparatus 10, or may be provided on a wall, a ceiling, or the like of an imaging room in which the imaging apparatus 10 is disposed.

In addition, the optical camera 8 optically images a portion that is not included in the medical image of the examinee. Specifically, the breast is included as the subject in the radiation image and the ultrasound image obtained by the imaging apparatus 10. However, in a case in which the radiography or the ultrasound imaging is performed on the breast in the compressed state, the shape and the position of the breast imaged in the image may be changed in accordance with a compression pressure, a compression thickness, a positioning method, a state of the breast during the imaging, and the like. In addition, the shape of the breast containing a large amount of fat is likely to be changed in an order of time even in the same examinee, and a part of the breast may be excised by the treatment. Then, by using the optical camera 8 that captures the optical image including a physical feature of the examinee other than the breast as the subject of the medical image, particularly, a joint point of the examinee, utilization can be achieved for specifying a reference position that is unique to each examinee and has a small change (details will be described below).

Incidentally, for example, in a case in which the same breast is imaged a plurality of times for follow-up observation, regular examination, and the like, it may be difficult to perform the comparative image interpretation because the appearance of the breast is different. In addition, in a case in which the comparative image interpretation is performed by combining a plurality of different types of medical images of the mammography, the ultrasound imaging, the CT, the MRI, and the like, the appearance of the breast imaged in each image is different, and thus it may be difficult to perform the comparative image interpretation.

Then, the console 50 according to the present embodiment specifies, for each medical image, the reference position estimated to be common between the medical images based on the optical image obtained by the optical camera 8, and performs the registration between the plurality of medical images based on the reference position. Accordingly, it is possible to perform the registration for the plurality of medical images related to the same subject even in a case in which the subject portions do not completely match each other or the states of the subject portions do not completely match each other. Hereinafter, a description of the console 50 will be made.

Figure 5:
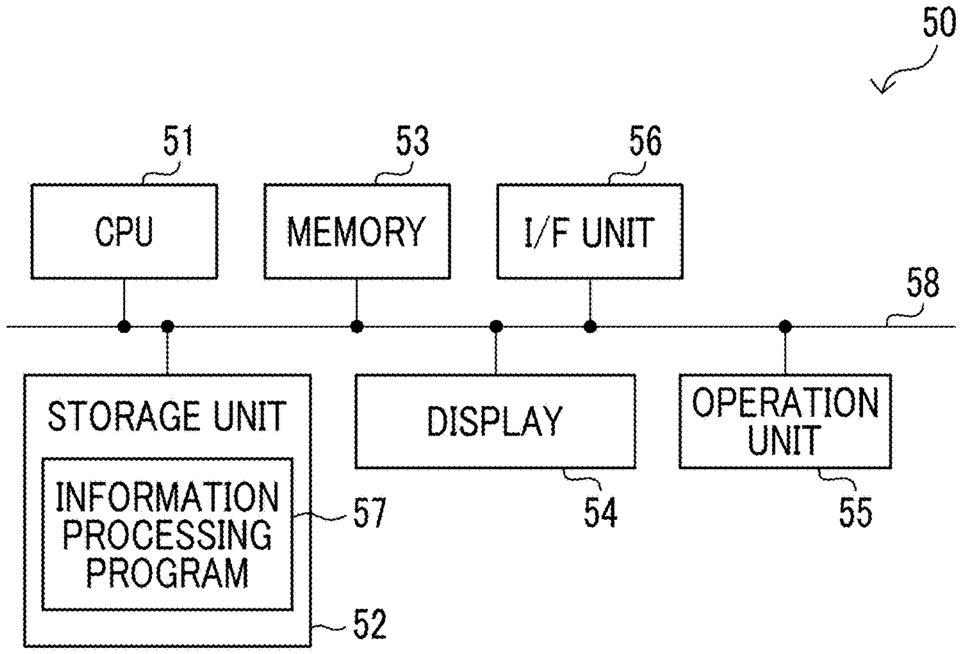
FIG. 5 is a block diagram showing an example of a hardware configuration of a console.

A description of an example of a hardware configuration of the console 50 will be made with reference to FIG. 5. As shown in FIG. 5, the console 50 includes a CPU 51, a non-volatile storage unit 52, and a memory 53 as a transitory storage region. In addition, the console 50 includes a display 54, such as a liquid crystal display, an operation unit 55, such as a touch panel, a keyboard, and a mouse, and an I/F unit 56. The I/F unit 56 performs wired or wireless communication with the optical camera 8, the imaging apparatus 10, the RIS 6, and other external apparatuses. The CPU 51, the storage unit 52, the memory 53, the display 54, the operation unit 55, and the I/F unit 56 are connected to each other via a bus 58, such as a system bus and a control bus, so that various types of information can be exchanged.

The storage unit 52 is realized by, for example, a storage medium, such as an HDD, an SSD, and a flash memory. A information processing program 57 in the console 50 is stored in the storage unit 52. The CPU 51 reads out the information processing program 57 from the storage unit 52 to deploy the information processing program 57 into the memory 53, and executes the deployed information processing program 57. As the console 50, for example, a personal computer, a server computer, a smartphone, a tablet terminal, a wearable terminal, or the like can be applied as appropriate.

In addition, the storage unit 52 stores the optical image captured by the optical camera 8, the image data of the radiation image and the ultrasound image acquired by the imaging apparatus 10, various types of other information, and the like. The image data of the optical image, the radiation image, and the ultrasound image may be stored in association with at least one of the imaging order or the imaging information. The imaging information may be, for example, at least one of examinee information and an imaging item that are included in the imaging order, photographer information indicating a photographer (for example, the user, such as the doctor or the technician) who performs the imaging, or date and time information indicating date and time when the imaging is performed.

Figure 6:
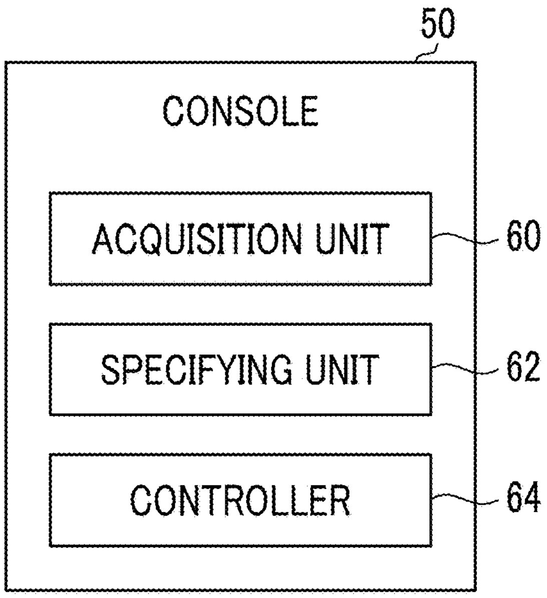
FIG. 6 is a block diagram showing an example of a functional configuration of the console.
Figure 8:
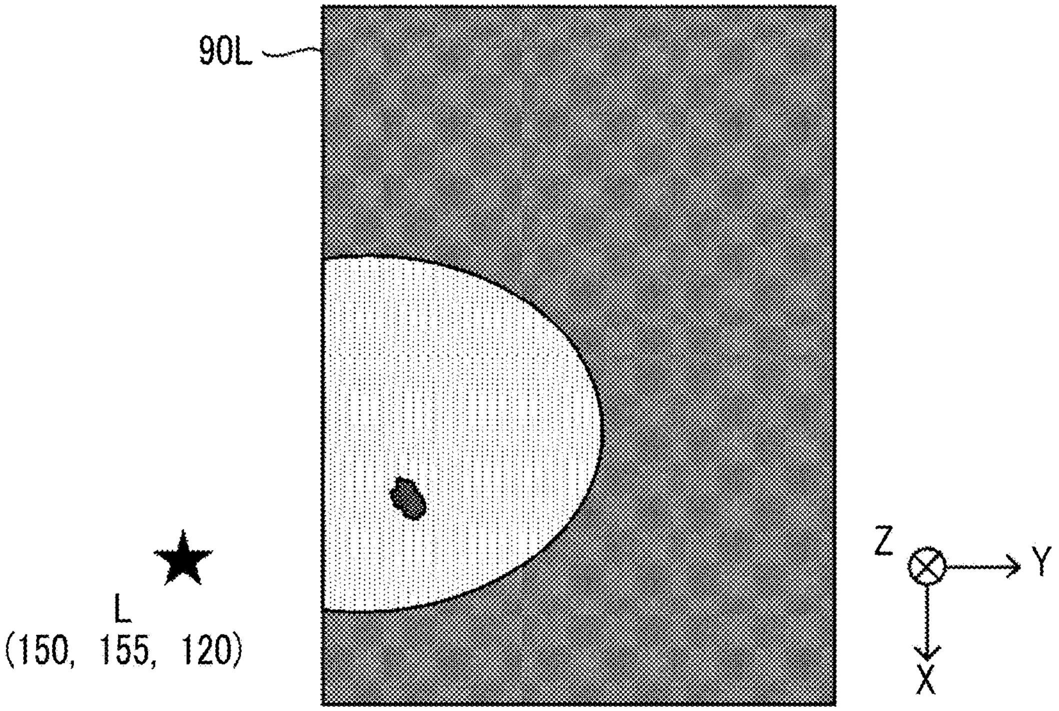
FIG. 8 is a view showing an example of a first medical image according to a first example.

A description of an example of a functional configuration of the console 50 will be made with reference to FIG. 6. As shown in FIG. 8, the console 50 includes an acquisition unit 60, a specifying unit 62, and a controller 66. In a case in which the CPU 51 executes the information processing program 57, the CPU 51 functions as the acquisition unit 60, the specifying unit 62, and the controller 66.

First Example

A description of a first example will be made with reference to FIGS. 7 to 10. The first example is an example of a case in which the radiography is performed twice with a left breast of a certain examinee as the subject.

The acquisition unit 60 acquires a first optical image of the examinee captured at a certain first point in time, from the optical camera 8. FIG. 7 shows, as an example of the first optical image, a visible light image 80 obtained by imaging an examinee H from the upper side of the head of the examinee H. The examinee H and the imaging apparatus 10 are imaged in the visible light image 80 of FIG. 7. It should be noted that, in FIG. 7, for the sake of description, a skin line of the left breast and a region of the radiation detector 28 that are not imaged in the visible light image 80 are shown by dotted lines.

In addition, the acquisition unit 60 acquires the first medical image of the examinee captured at the first point in time from the imaging apparatus 10. Specifically, the acquisition unit 60 may acquire the first medical image stored in the storage unit 22 of the imaging apparatus 10 via the I/F unit 56, may acquire the first medical image stored in the storage unit 52, or may acquire the first medical image stored in the external apparatus. FIG. 8 shows a mammography image 90L of the left breast put into the compressed state as an example of the first medical image.

It should be noted that the "first points in time" at which the first medical image and the first optical image are captured are substantially the same points in time, does not have to be at the completely same point in time, and may have a time width (for example, about 1 minute). That is, it is sufficient that the state (posture, position, and the like) of the examinee at an imaging point in time of the first medical image is substantially the same as the state of the examinee at an imaging point in time of the first optical image, and a temporal deviation in the imaging timing is allowed.

The specifying unit 62 specifies at least one first reference position based on the physical feature of the examinee included in the first optical image. The "first reference position" is unique to each examinee, and is an indicator that has a small change due to a time, a method, a position, a posture, a physical state, and the like of the imaging. Hereinafter, the description will be made by indicating the first reference position by one three-dimensional point (X coordinate, Y coordinate, and Z coordinate), but the present disclosure is not limited to this, and the first reference position may be indicated one-dimensionally or two-dimensionally. The number of the first reference positions is not particularly limited and may be plural.

The "physical feature of the examinee" is, for example, the joint point of the examinee. The specifying unit 62 may extract the joint point of the examinee based on the first optical image, and may specify the first reference position in accordance with the joint point. For example, in FIG. 7, a right shoulder and a left shoulder of the examinee H are shown as the joint points by black points. The specifying unit 62 may specify a center (150) of the right shoulder and the left shoulder in the X direction in FIG. 7 as the X coordinate of a first reference position L. Similarly, the specifying unit 62 may specify a center (155) of the right shoulder and the left shoulder in the Y direction in FIG. 7 as the Y coordinate of the first reference position L. It should be noted that, as a method of extracting the joint point, a known posture estimation technique or the like can be applied as appropriate.

In addition, for example, the specifying unit 62 may specify the Z coordinate of the first reference position as the height from a floor surface of the imaging room in which the imaging apparatus 10 is disposed, to the breast of the examinee. The height from the floor surface to the breast of the examinee can be calculated by, for example, the sum of a known height from the floor surface to the imaging surface 16A of the imaging apparatus 10 and the compression thickness (height from the imaging surface 16A to the contact surface 43B of the compression member 40) at the first point in time. The compression thickness can be measured by, for example, installing a sensor, such as a linear potentiometer, in the compression member 40 or the like.

The controller 64 associates the first medical image acquired by the acquisition unit 60 with the first reference position specified by the specifying unit 62. In a case in which the first medical image is stored in the storage medium, such as the storage unit 52, the controller 64 stores the first medical image together with the associated first reference position. For example, as indicated by star marks in FIG. 8, the X coordinate, the Y coordinate, and the Z coordinate of the first reference position L are specified by the specifying unit 62 as (X, Y, Z)=(150, 155, 120). In this case, the controller 64 stores the mammography image 90L and the information indicating that the first reference position Lis (X, Y, Z)=(150, 155, 120) in the storage unit 52 in association with each other.

Similarly to the first medical image and the first optical image, the acquisition unit 60 acquires a second medical image and a second optical image of the examinee captured at a second point in time. The "second points in time" at which the second medical image and the second optical image are captured are substantially the same points in time, does not have to be at the completely same point in time, and may have a time width (for example, about 1 minute). In addition, the second point in time may be substantially the same as or different from the first point in time.

Similarly to the first reference position, the specifying unit 62 specifies at least one second reference position based on the physical feature of the examinee included in the second optical image. For example, the specifying unit 62 may specify the joint point of the examinee included in the second optical image, and may specify the second reference position in accordance with the joint point. Similarly to the first reference position, the "second reference position" is also unique to each examinee, and is an indicator that has a small change due to the time, the method, the position, the posture, the physical state, and the like of the imaging. Therefore, the second reference position indicates the first reference position (itself) or substantially the same position as the first reference position.

Similarly to the first medical image and the first reference position, the controller 64 associates the second medical image acquired by the acquisition unit 60 with the second reference position specified by the specifying unit 62. In a case in which the second medical image is stored in the storage medium, such as the storage unit 52, the controller 64 stores the second medical image together with the associated second reference position.

Figure 9:
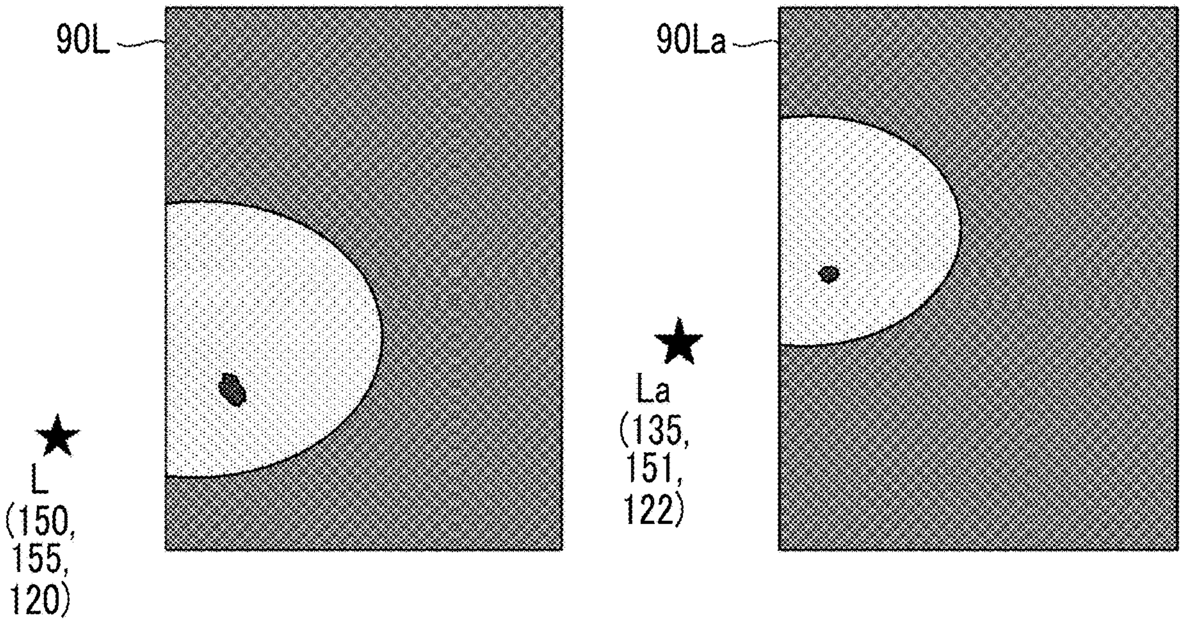
FIG. 9 is a view showing an example of the first medical image and a second medical image according to the first example.

FIG. 9 shows a mammography image 90La as an example of the second medical image, and a second reference position La as an example of the second reference position. FIG. 9 shows the mammography image 90L of FIG. 8 and the first reference position L side by side for reference. The mammography image 90La is an image of the left breast put into the compressed state, and is obtained by imaging the same subject as the subject of the mammography image 90L at different imaging points in time. The second reference position La is specified as (X, Y, Z)=(135, 151, 122).

The subjects of the mammography images 90L and 90La are the same, but the appearance of the breast imaged in each image is different as shown in FIG. 9. This is because the position, the posture, and the physical state of the examinee are different, or the compression pressure, the compression thickness, and the positioning method are different. On the other hand, the first reference position L and the second reference position La should be unique to each examinee, have a small change, and indicate substantially the same positions.

Then, the controller 64 outputs a result of associating the first medical image with the second medical image based on the first reference position and the second reference position. For example, the controller 64 may perform control of storing the result of associating the first medical image with the second medical image in the storage medium, such as the storage unit 52.

Figure 10:
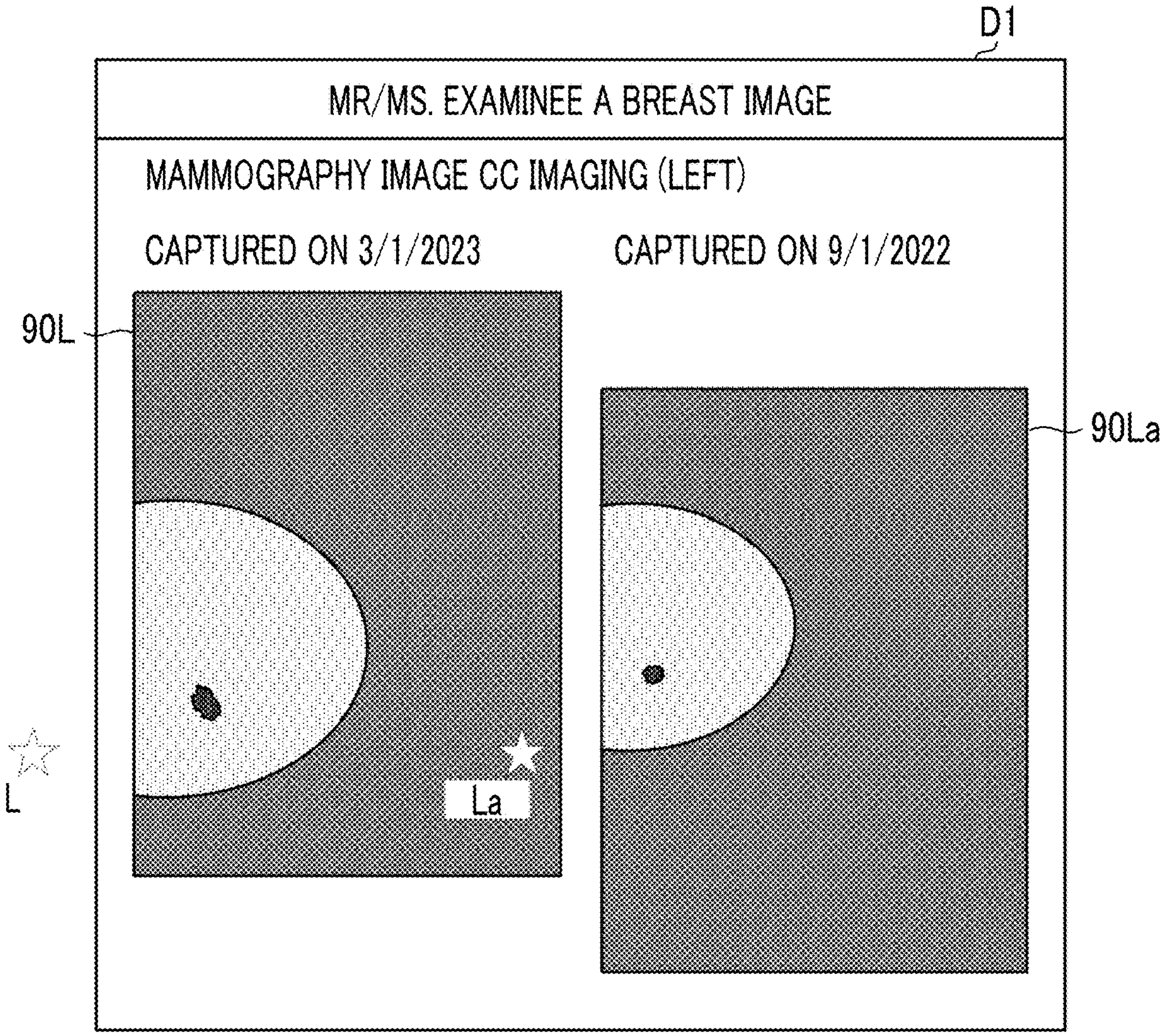
FIG. 10 is a view showing an example of a screen displayed on a display according to the first example.

In addition, for example, the controller 64 may perform control of performing the registration between the first medical image and the second medical image based on the first reference position and the second reference position, to display the first medical image and the second medical image on the display 54. FIG. 10 shows an example of a screen D1 displayed on the display 54 by the controller 64. As shown in FIG. 10, the controller 64 may display the mammography images 90L and 90La on the display 54 by aligning the X coordinates of the first reference position L and the second reference position La with each other. In this case, the comparative image interpretation is facilitated. It should be noted that the first reference position L and the second reference position La indicated by star marks in FIG. 10 are shown for description, and are not included in the screen D1.

In addition, for example, the controller 64 may perform control of performing the registration between the first medical image and the second medical image based on the first reference position and the second reference position, to print the first medical image and the second medical image on paper by using an external printer. In addition, for example, the controller 64 may perform control of outputting the result of associating the first medical image with the second medical image to another external apparatus via a network or the like. In this way, the unit that outputs the result of associating the first medical image with the second medical image is not particularly limited.

Second Example

Figure 11:
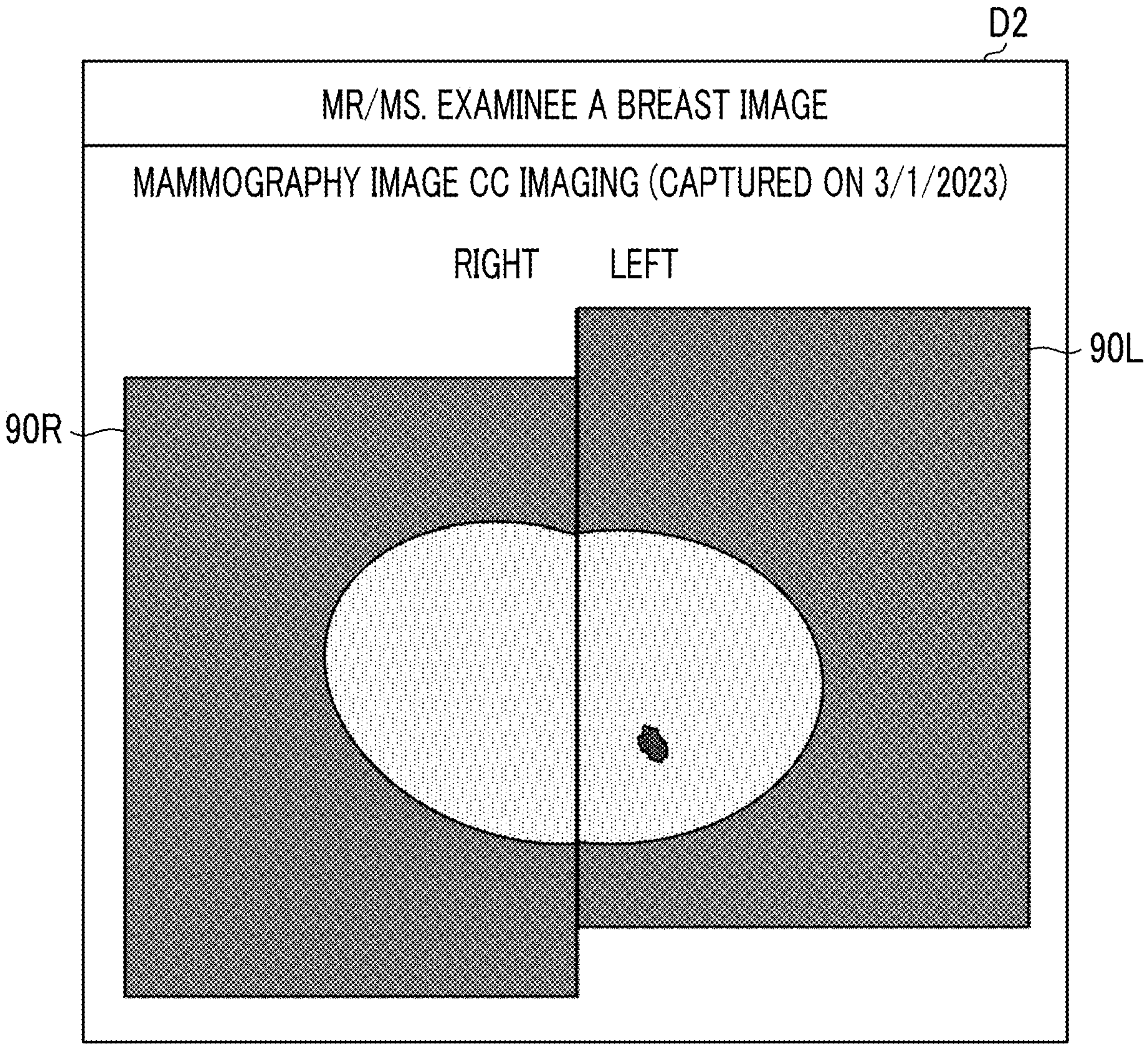
FIG. 11 is a view showing an example of a screen displayed on a display according to a second example.

A description of a second example will be made with reference to FIG. 11. The second example is an example of a case in which the radiography is performed with each of the left and right breasts of a certain examinee as the subject. FIG. 11 is an example of a screen D2 displayed on the display 54 by the controller 64. In the description of each of the following examples, the description overlapping the first example will be omitted.

The acquisition unit 60 acquires the mammography image 90L of the left breast of the examinee as the first medical image captured at the first point in time. In addition, the acquisition unit 60 acquires a mammography image 90R of the right breast of the examinee as the second medical image captured at the second point in time. In addition, the acquisition unit 60 acquires the first optical image at the first point in time and the second optical image at the second point in time.

The specifying unit 62 specifies the first reference position based on the first optical image, and specifies the second reference position based on the second optical image. The mammography images 90L and 90R are the left and right breasts in which the subjects are different from each other, but the first reference position and the second reference position are unique to each examinee and do not depend on the subject of the mammography image.

The controller 64 associates the mammography image 90L of the left breast acquired by the acquisition unit 60 with the first reference position specified by the specifying unit 62. The controller 64 associates the mammography image 90R of the right breast acquired by the acquisition unit 60 with the second reference position specified by the specifying unit 62. Further, the controller 64 outputs a result of associating the mammography image 90L with the mammography image 90R based on the first reference position and the second reference position. For example, as shown in FIG. 11, the controller 64 performs control of performing the registration between the mammography images 90L and 90R based on the first reference position and the second reference position, to display the mammography images 90L and 90R on the display 54. In this way, even in a case in which the subject portions do not completely match, such as the right breast and the left breast, the registration is performed, whereby the comparative image interpretation is facilitated.

Third Example

Figure 12:
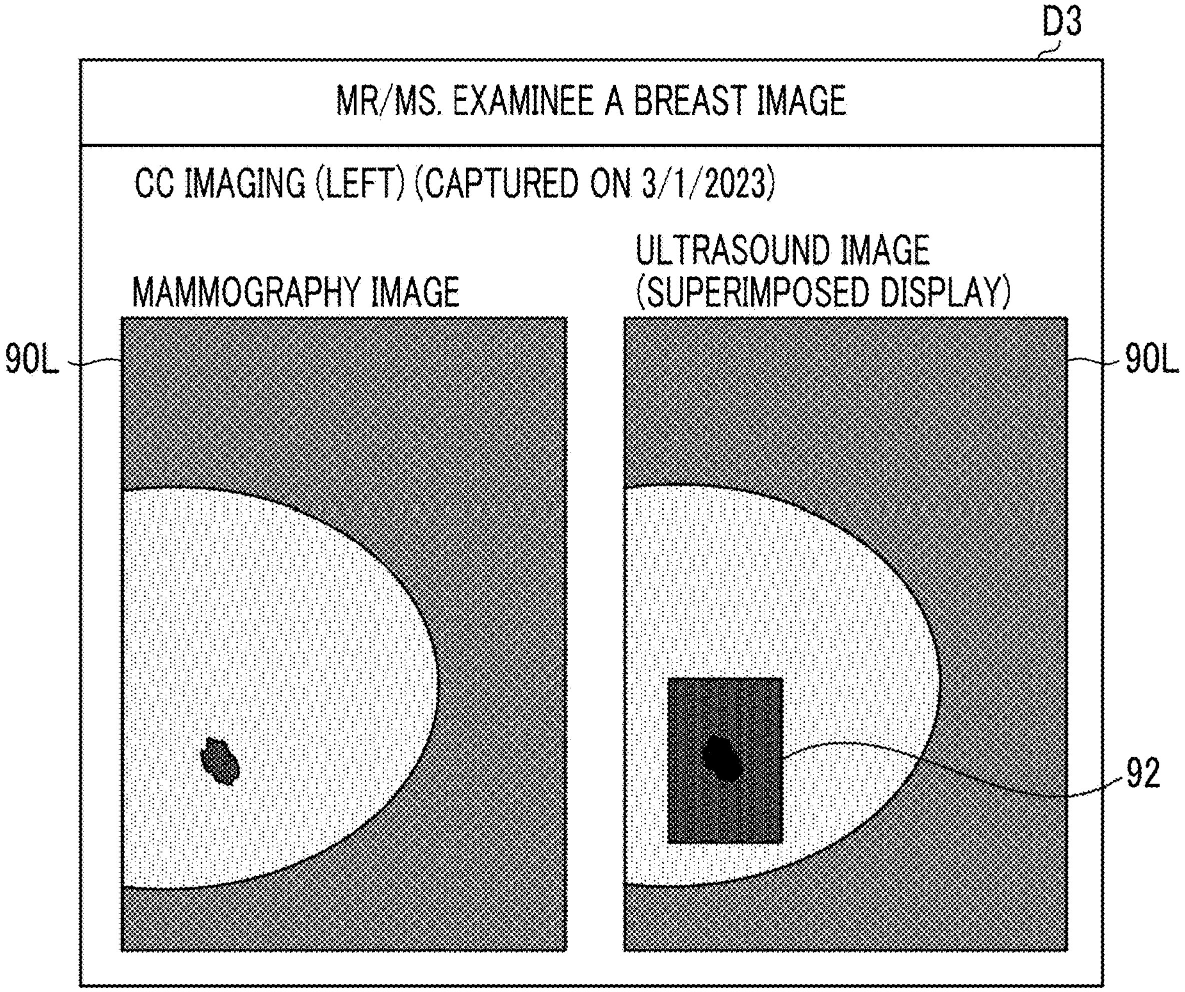
FIG. 12 is a view showing an example of a screen displayed on a display according to a third example.

A description of a third example will be made with reference to FIG. 12. The third example is an example of a case in which the radiography and the ultrasound imaging are performed with the left breast of a certain examinee as the subject. FIG. 12 is an example of a screen D3 displayed on the display 54 by the controller 64.

The acquisition unit 60 acquires the mammography image 90L of the left breast of the examinee as the first medical image captured at the first point in time. In addition, the acquisition unit 60 acquires the ultrasound image 92 of the left breast of the examinee that is captured by the ultrasound probe 30 as the second medical image that is captured at the second point in time. In addition, the acquisition unit 60 acquires the first optical image at the first point in time and the second optical image at the second point in time. It should be noted that, as described above, the first point in time and the second point in time may be substantially the same point in time or different points in time.

It is preferable that the ultrasound image 92 is an image showing the same tomographic plane (XY plane) as the mammography image 90L. In FIG. 2, the ultrasound image captured by the ultrasound probe 30 is an image showing an XZ plane or a YZ plane. A three-dimensional ultrasound image is obtained by capturing a plurality of ultrasound images showing the XZ plane or YZ plane while changing an imaging range, and reconstructing the ultrasound images. The ultrasound image showing the XY plane can be generated from the three-dimensional ultrasound image.

The specifying unit 62 specifies the first reference position based on the first optical image, and specifies the second reference position based on the second optical image.

Meanwhile, as shown in FIG. 2 and the like, in the imaging apparatus 10, the ultrasound imaging is performed by the ultrasound probe 30 via the compression member 40. In a case in which the imaging range at one time (that is, in a fixed state) is smaller than the breast as the subject and the entire breast is subjected to the ultrasound imaging, it is necessary for the ultrasound probe 30 to scan the upper surface 43A of the compression member 40 to perform the imaging. On the other hand, in some cases, a part of the breast is imaged by the ultrasound probe 30 in order to reduce the imaging time (see FIG. 12). In this case, for the registration between the images, it is necessary to specify the position at which the ultrasound probe 30 is disposed on the upper surface 43A of the compression member 40 to perform the imaging, in addition to the second reference position based on the second optical image.

Therefore, the specifying unit 62 may specify the position of the ultrasound probe 30 at a point in time at which the user, such as the doctor or the technician, performs the imaging while fixing the position of the ultrasound probe 30. For example, at the point in time at which the user fixes the position of the ultrasound probe 30, the notification of the fact may be given via the operation unit 55, and the specifying unit 62 that receives the notification may acquire the position of the ultrasound probe 30 at the point in time.

For example, the position of the ultrasound probe 30 may be measured by installing a distance measurement sensor that measures the distance to the subject in the arm part 12 or the like of the imaging apparatus 10, and using the distance measurement sensor. As the distance measurement sensor, for example, a laser imaging detection and ranging or light detection and ranging (LIDAR), a time-of-flight (TOF) camera, a stereo camera, or the like can be applied. The LIDAR and the TOF camera emit light, such as infrared light and visible light, and measure a distance based on a time until the reflected light is received or a phase change between the emitted light and the received light. The LIDAR measures a distance to an object to be measured by disposing a plurality of laser light emitters in a vertical direction and allowing each of the emitters to perform horizontally scanning (rotating). The TOF camera measures the distance to the object to be measured by emitting diffused light. The stereo camera measures the distance to the object to be measured by using a principle of triangulation based on a plurality of images obtained by imaging the object to be measured in different directions.

In addition, for example, the position of the ultrasound probe 30 may be measured by installing a meter that measures the movement amount from a predetermined position in the support part 36 of the imaging apparatus 10 or the like, and using the meter. For example, a potentiometer and the like can be applied as such a meter.

In addition, for example, the position of the ultrasound probe 30 may be measured by installing a digital camera in the arm part 12 or the like, and performing image recognition based on the visible light image obtained by imaging the entire compression member 40 and the ultrasound probe 30. In this case, a marker for image recognition may be provided in the ultrasound probe 30 to improve the accuracy of image recognition. As the marker for image recognition, an illumination display, such as a light emitting diode (LED), may be used. In this case, the LED may emit light or change color only in a period in which the ultrasound probe 30 is fixed, or may emit light or change color only in a predetermined period after the notification is given to the specifying unit 62 that the position of the ultrasound probe 30 is fixed by the user.

The controller 64 associates the mammography image 90L acquired by the acquisition unit 60 with the first reference position specified by the specifying unit 62. In addition, the controller 64 associates the ultrasound image 92 acquired by the acquisition unit 60, the second reference position specified by the specifying unit 62, and the position of the ultrasound probe 30 with each other.

The controller 64 outputs the result of associating the mammography image 90L with the ultrasound image 92 based on the first reference position, the second reference position, and the position of the ultrasound probe 30. For example, as shown in FIG. 12, the controller 64 may perform control of performing the registration between the mammography image 90L and the ultrasound image 92 based on the first reference position, the second reference position, and the position of the ultrasound probe 30, to display the mammography image 90L and the ultrasound image 92 on the display 54. In the example of FIG. 12, the ultrasound image 92 is displayed in a state of being superimposed on the mammography image 90L. In this way, even in a case in which the subject portions do not completely match, the registration is performed, whereby the comparative image interpretation is facilitated.

It should be noted that the ultrasound probe 30 can perform the ultrasound imaging by setting an angle with respect to the upper surface 43A of the compression member 40. Then, the specifying unit 62 may specify an orientation (angle) of the ultrasound probe 30, in addition to the second reference position and the position of the ultrasound probe 30. The orientation of the ultrasound probe may be measured by, for example, providing a magnetic sensor or an acceleration sensor (gyro sensor) in the ultrasound probe 30. In addition, the orientation of the ultrasound probe may be measured by, for example, performing image recognition based on the visible light image.

The controller 64 associates the ultrasound image 92 acquired by the acquisition unit 60, the second reference position specified by the specifying unit 62, the position of the ultrasound probe 30, and the orientation of the ultrasound probe 30 with each other. In a case in which the orientation of the ultrasound probe 30 is changed, the imaging range of the ultrasound image 92 is also changed. Therefore, the controller 64 performs the registration between the mammography image 90L and the ultrasound image 92 based on the first reference position, the second reference position, the position of the ultrasound probe 30, and the orientation of the ultrasound probe 30.

It should be noted that, in a case in which the entire breast is subjected to the ultrasound imaging by scanning the ultrasound probe 30 over the entire surface of the compression member 40, specifying the position and the orientation of the ultrasound probe 30 can be omitted.

Fourth Example

Figure 13:
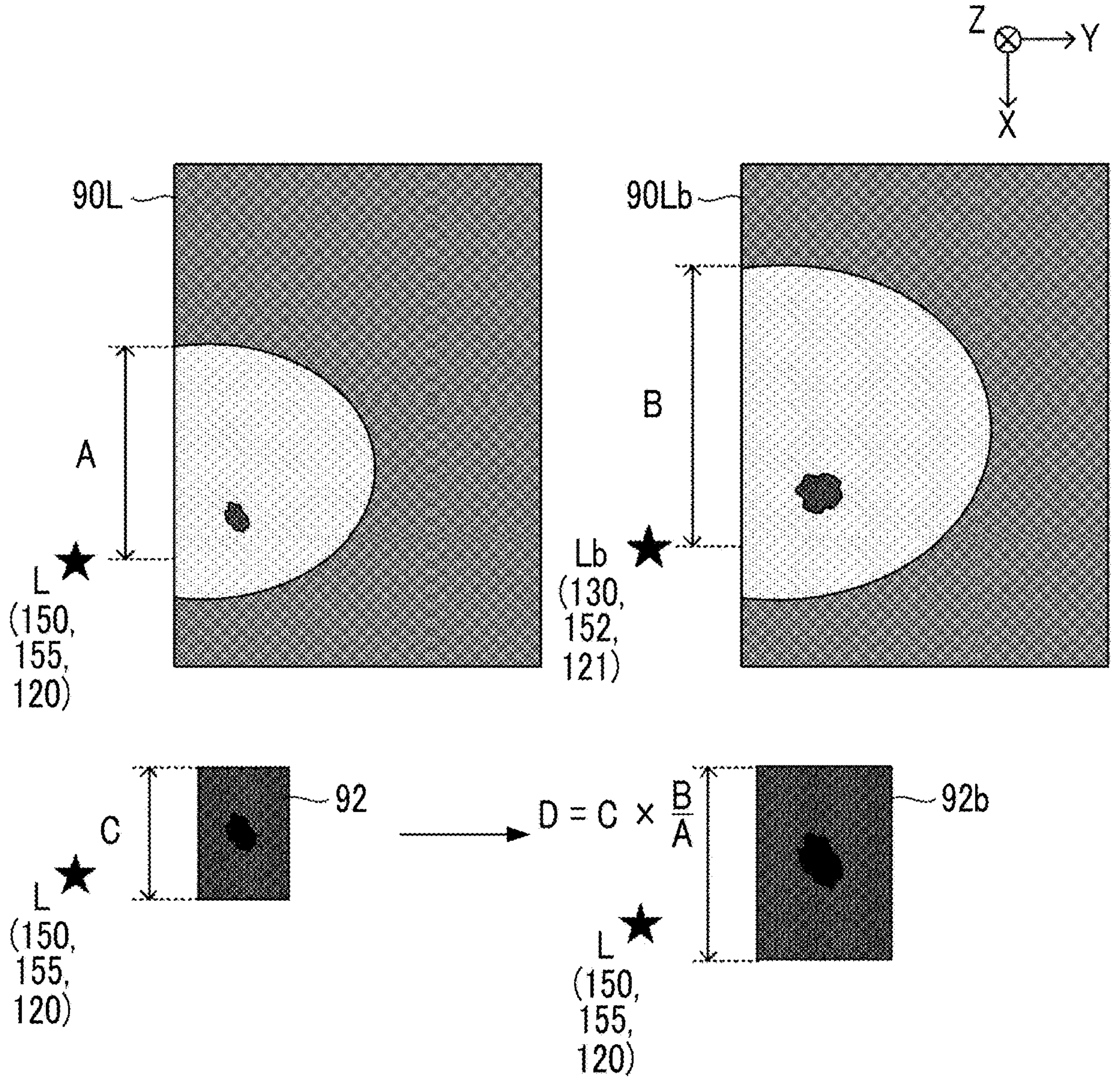
FIG. 13 is a view showing an example of a correction image according to a fourth example.

A description of a fourth example will be made with reference to FIG. 13. The fourth example is an example in which the radiography is performed twice with the left breast of a certain examinee as the subject, the ultrasound imaging is performed in the first radiography, and the ultrasound imaging is not performed in the second radiography. In this case, in some cases, it is possible to support the comparative image interpretation by performing the registration between the first ultrasound image and the second radiation image.

However, since the appearance of the breast in the radiation image is different each time, it is desired to correct the ultrasound image and then perform the registration. FIG. 13 shows the first mammography image 90L, the first ultrasound image 92, a second mammography image 90Lb, and a correction image 92*b* obtained by correcting the first ultrasound image 92 in accordance with the second mammography image 90Lb.

The acquisition unit 60 acquires the mammography image 90L of the left breast of the examinee as the first medical image captured at the first point in time. In addition, the acquisition unit 60 acquires the mammography image 90Lb of the left breast of the examinee as the second medical image captured at the second point in time. It should be noted that the appearances of the breasts imaged in the mammography images 90L and 90La are different, but the subjects are the same. In addition, the acquisition unit 60 acquires the ultrasound image 92 of the left breast of the examinee captured by the ultrasound probe 30 at the first point in time.

In addition, the acquisition unit 60 acquires the first optical image at the first point in time and the second optical image at the second point in time. The specifying unit 62 specifies the first reference position L based on the first optical image, and specifies the second reference position Lb based on the second optical image.

The controller 64 generates the correction image (ultrasound image) 92*b* suitable for the second mammography image 90Lb based on the first ultrasound image 92. For example, in the X direction of FIG. 13, the controller 64 derives a distance A from one end of the skin line of the breast included in the first mammography image 90L to the first reference position L. Similarly, the controller 64 derives a distance B from one end of the skin line of the breast included in the second mammography image 90Lb to the second reference position Lb.

The controller 64 derives a width D of the correction image 92*b* in the X direction estimated as the second ultrasound image based on a ratio between the distances A and B, and a width C of the first ultrasound image 92 in the X direction, based on the following expression.

$$D=C\times B/A$$

Thereafter, the controller 64 generates the correction image 92*b* by magnifying or reducing the first ultrasound image 92 so that the width of the first ultrasound image 92 in the X direction is D. It should be noted that, in this case, a relative positional relationship between the ultrasound image 92 and the first reference position L and a relative positional relationship between the correction image 92*b* and the first reference position L are not changed.

The controller 64 associates the first mammography image 90L acquired by the acquisition unit 60, the ultrasound image 92, and the first reference position L specified by the specifying unit 62 with each other. In addition, the controller 64 associates the second mammography image 90Lb acquired by the acquisition unit 60, the second reference position Lb specified by the specifying unit 62, and the correction image 92*b* with each other.

In addition, the controller 64 performs the registration between the second mammography image 90Lb and the correction image 92*b*. In this case, the controller 64 performs the registration based on the second reference position Lb associated with the second mammography image 90Lb, and the first reference position L associated with the correction image 92*b*. In this way, by performing the registration of the image (correction image 92*b*) obtained by correcting the first ultrasound image 92 with respect to the second mammography image 90Lb, the comparative image interpretation is facilitated.

Fifth Example

Figure 14:
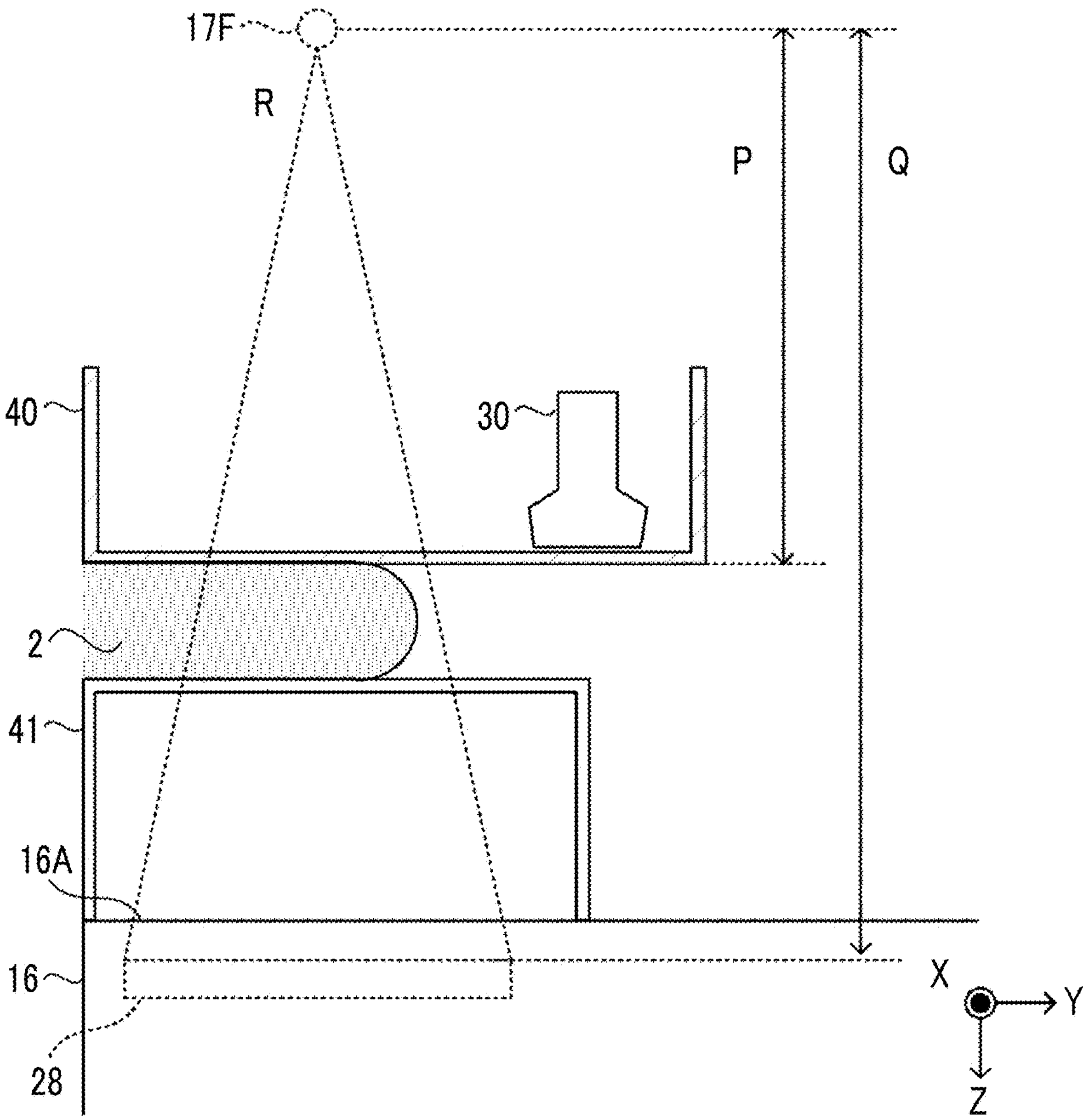
FIG. 14 is a schematic view of magnification radiography.

A description of a fifth example will be made with reference to FIGS. 14 and 15. The fifth example is an example of a case in which normal radiography and magnification radiography are performed with the left breast of a certain examinee as the subject. FIG. 14 is a view showing an outline of the magnification radiography. As shown in FIG. 14, the breast can be magnified and imaged by irradiating the breast with the radiation R to perform the imaging by using a table 41 in a state in which the radiation detector 28 and the breast 2 as the subject are separated from each other. In a case in which a normal radiation image and the image obtained by the magnification radiography are subjected to the comparative image interpretation, it may be easier to see the images by resolving the difference in the magnification ratio and performing the registration.

Figure 15:
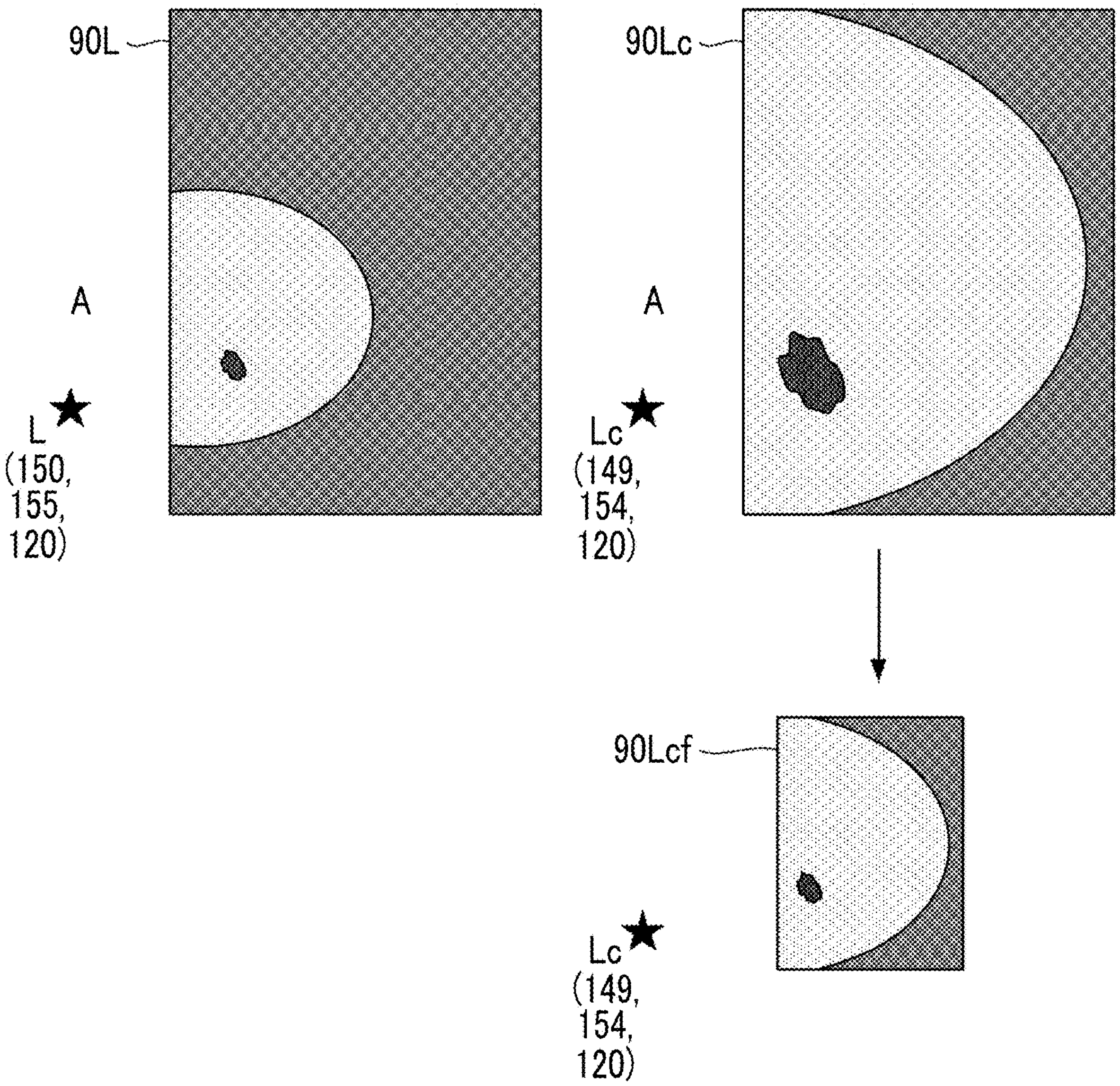
FIG. 15 is a view showing an example of a correction image according to a fifth example.

FIG. 15 shows the normal mammography image 90L captured in a state in which the breast 2 is in contact with the imaging surface 16A, a magnification mammography image 90Lc obtained by the magnification radiography, and a correction image 90Lcf in which the scale of the magnification mammography image 90Lc is corrected.

The acquisition unit 60 acquires the mammography image 90L of the left breast of the examinee as the first medical image captured at the first point in time. In addition, the acquisition unit 60 acquires the magnification mammography image 90Lc of the left breast of the examinee as the second medical image captured at the second point in time. Hereinafter, a distance from a focus of the radiation source 17R to the breast 2 as the subject will be referred to as an imaging distance. In a case in which the mammography image L is captured by setting the imaging distance to a first distance, it can be said that the magnification mammography image 90Lc is captured by setting the imaging distance as a second distance shorter than the first distance. It should be noted that the appearances of the breasts imaged in the mammography images 90L and 90La shown in FIG. 15 are different, but the subjects are the same.

In addition, the acquisition unit 60 acquires the first optical image at the first point in time and the second optical image at the second point in time. The specifying unit 62 specifies the first reference position L based on the first optical image, and specifies the second reference position Lc based on the second optical image.

The controller 64 derives a magnification ratio M of the magnification mammography image 90Lc based on the second distance, and generates the correction image (mammography image) 90Lcf in which the scale of the magnification mammography image 90Lc is matched with the mammography image 90L. As shown in FIG. 14, the magnification ratio M of the magnification mammography image 90Lc can be derived based on the following expression using a distance P from a focus 17F of the radiation source 17R to the subject (breast 2) and a distance Q from the focus 17F to a detection surface of the radiation detector 28. The distance P is a known value for each imaging apparatus 10. The distance Q can be calculated by, for example, installing a sensor, such as a linear potentiometer, in the compression member 40 or the like and measuring the compression thickness.

$$M=Q/P$$

The controller 64 reduces the magnification mammography image 90Lc to be the same as the magnification ratio of the mammography image 90L based on the derived magnification ratio M, to obtain the correction image 90Lcf. It should be noted that, in this case, a relative positional relationship between the magnification mammography image 90Lc and the second reference position Lc and a relative positional relationship between the correction image 90Lcf and the second reference position Lc are not changed.

The controller 64 associates the mammography image 90L acquired by the acquisition unit 60 with the first reference position L specified by the specifying unit 62. Also, the controller 64 associates the magnification mammography image 90Lc acquired by the acquisition unit 60, the second reference position Lc specified by the specifying unit 62, and the correction image 90Lcf with each other.

The controller 64 outputs a result of associating the mammography image 90L with the correction image 90Lcf (reduced magnification mammography image 90Lc). For example, the controller 64 performs the registration based on the first reference position L associated with the mammography image 90L and the second reference position Lc associated with the magnification mammography image 90Lc. As described above, there is a case in which the comparative image interpretation is facilitated by performing the registration between the normal mammography image 90L and the correction image 90Lcf (magnification mammography image) after matching the scales.

Sixth Example

A sixth example is an example in which the same magnification radiography and the ultrasound imaging as in the fifth example are performed. As shown in FIG. 14, even in a case in which the breast 2 is positioned by using the table 41 for the magnification radiography, the distance between the ultrasound probe 30 and the breast 2 is the same as in a case in which the normal radiography is performed without using the table 41, so that the magnification of the obtained ultrasound image is not changed. Therefore, in a case in which the image obtained by the magnification radiography and the ultrasound image are subjected to the comparative image interpretation, it may be easier to see the images by performing the registration after reducing the image obtained by the magnification radiography in accordance with the magnification ratio.

The acquisition unit 60 acquires the magnification mammography image 90Lc of the left breast of the examinee as the first medical image captured at the first point in time. In addition, the acquisition unit 60 acquires the ultrasound image 92 of the left breast of the examinee that is captured by the ultrasound probe 30 as the second medical image that is captured at the second point in time.

In addition, the acquisition unit 60 acquires the first optical image at the first point in time and the second optical image at the second point in time. As in the fifth example, the specifying unit 62 specifies the first reference position L based on the first optical image, and specifies the second reference position Le based on the second optical image. In addition, the specifying unit 62 specifies the position and/or the orientation of the ultrasound probe 30 as in the third example.

As in the fifth example, the specifying unit 62 generates the correction image 90Lcf based on the magnification mammography image 90Lc. In addition, the controller 64 can performs the registration between the correction image 90Lcf and the ultrasound image 92 based on the first reference position L, the second reference position Lc, and the position of the ultrasound probe 30 and/or the orientation of the ultrasound probe 30. In this manner, there is a case in which the comparative image interpretation is facilitated by performing the registration between the ultrasound image 92 and the correction image 90Lcf (magnification mammography image) after matching the scales.

Figure 16:
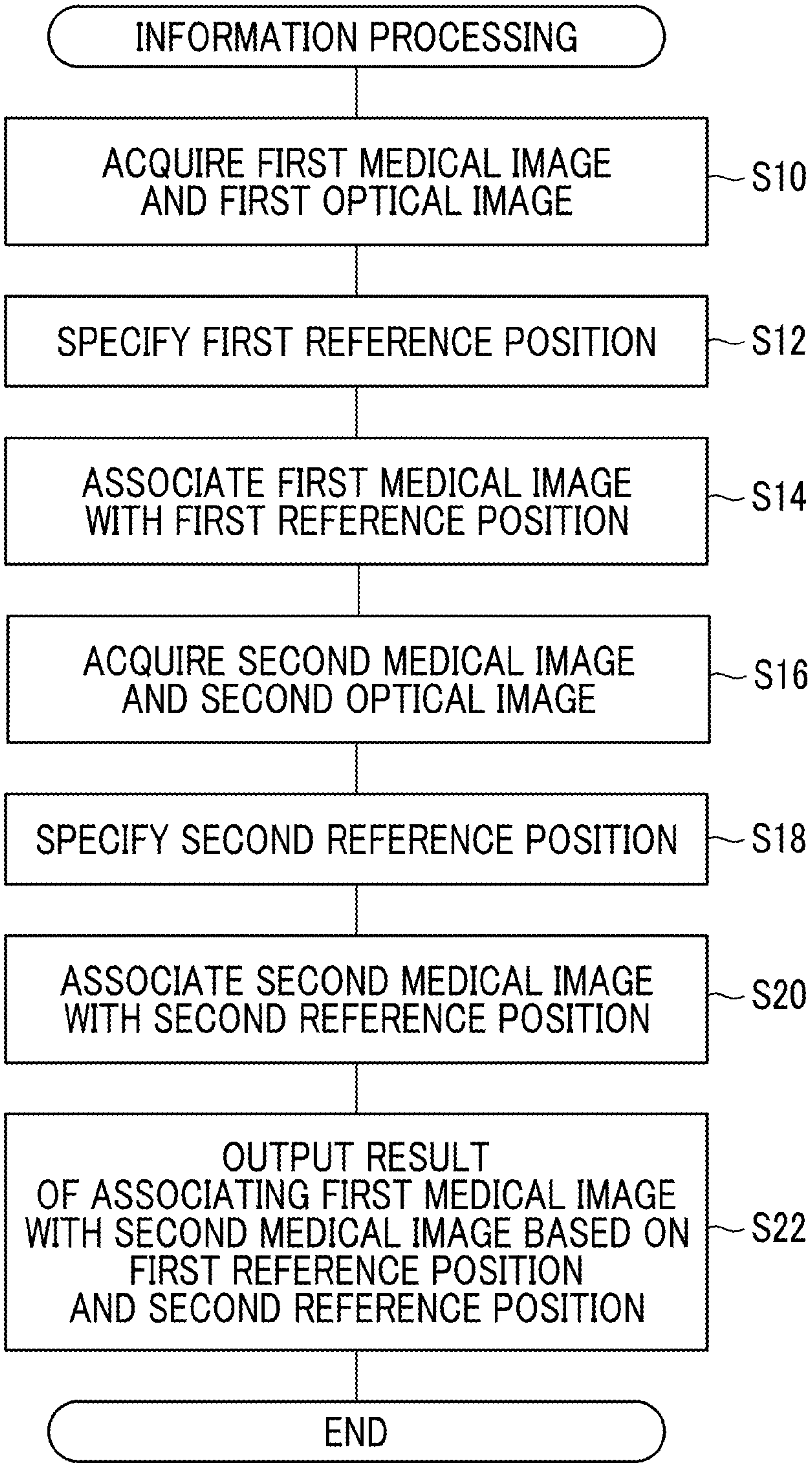
FIG. 16 is a flowchart showing an example of information processing.

Next, a description of an action of the console 50 according to the present embodiment will be made with reference to FIG. 16. In the console 50, the CPU 51 executes the information processing program 57 to execute a control process shown in FIG. 16. The control process is executed, for example, in a case in which the user gives an instruction to start the execution via the operation unit 55.

In step S10, the acquisition unit 60 acquires the first medical image of the examinee captured at the first point in time from the imaging apparatus 10. In addition, the acquisition unit 60 acquires the first optical image of the examinee captured at the first point in time from the optical camera 8. In step S12, the specifying unit 62 specifies at least one first reference position based on the physical feature of the examinee included in the first optical image acquired in step S10. In step S14, the controller 64 associates the first medical image acquired in step S10 with the first reference position specified in step S12.

In step S16, the acquisition unit 60 acquires the second medical image of the examinee captured at the second point in time from the imaging apparatus 10. In addition, the acquisition unit 60 acquires the second optical image of the examinee captured at the second point in time from the optical camera 8. In step S18, the specifying unit 62 specifies at least one second reference position based on the physical feature of the examinee included in the second optical image acquired in step S16. In step S20, the controller 64 associates the second medical image acquired in step S16 with the second reference position specified in step S18.

In step S22, the controller 64 outputs the result of associating the first medical image with the second medical image based on the first reference position and the first medical image which are associated with each other in step S14, and the second reference position and the second medical image which are associated with each other in step S18. For example, the controller 64 performs control of performing the registration between the first medical image and the second medical image, to display the first medical image and the second medical image on the display 54. In a case in which step S22 is completed, the present information processing is terminated.

As described above, the console 50 according to the aspect of the present disclosure includes at least one processor, in which the processor acquires the first medical image of the examinee associated with the first reference position specified based on the physical feature of the examinee included in the first optical image obtained by optically imaging the examinee, acquires the second medical image of the examinee associated with the first reference position or the second reference position indicating the position substantially the same as the first reference position, and outputs the result of associating the first medical image with the second medical image based on the first reference position and the second reference position.

With the console 50 according to the present embodiment, the reference position, which is unique to each examinee and has a small change due to the time, the method, the position, the posture, the physical state, and the like of the imaging, is associated with each medical image. Therefore, for example, in a case in which one subject is imaged a plurality of times or the imaging is performed by combining a plurality of different types of medical images of the mammography, the ultrasound imaging, the CT, the MRI, and the like for one subject, it is possible to perform the registration based on the reference position. That is, it is possible to perform the registration for the plurality of medical images related to the same subject even in a case in which the subject portions do not completely match each other or the states of the subject portions do not completely match each other.

Figure 17:
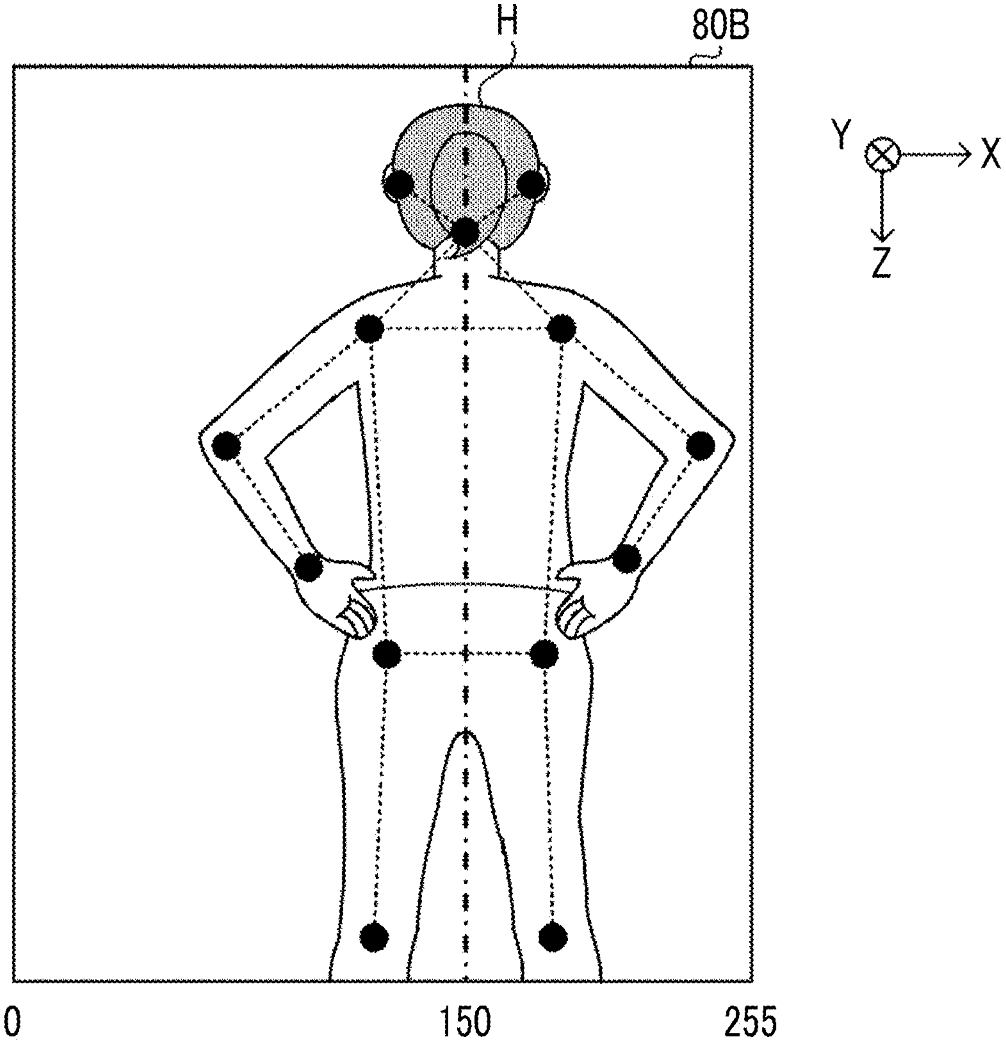
FIG. 17 is a view showing an example of the visible light image.

It should be noted that, in the embodiment described above, the form is described in which the optical camera 8 captures the visible light image of the examinee from the upper side of the head of the examinee, but the present disclosure is not limited to this. For example, the optical camera 8 may image the examinee from the back surface side of the examinee. In this case, for example, as shown in FIG. 17, a visible light image 80B in which the back surface side of the examinee is included is obtained. The specifying unit 62 can extract the joint points of the examinee based on the visible light image 80B, to specify the reference position based on a positional relationship between the joint points. For example, the specifying unit 62 may specify an average value of the centers of the combinations of the left and right joint points (for example, right car and left ear, right shoulder and left shoulder, right waist and left waist, or right knee and left knee) in the X direction, as the X coordinate of the reference position.

The optical camera 8 is not limited to an optical camera that captures the visible light image. For example, as the optical camera 8, a camera that captures a depth image may be applied. The depth image is an image composed of a pixel value indicating a distance from the optical camera 8 to the examinee, whereby a three-dimensional shape of the subject can be specified. For example, a LIDAR, a TOF camera, a stereo camera, or the like can be applied as the optical camera 8 that captures the depth image.

In addition, in the embodiment described above, the form is described in which the number of the optical cameras 8 is one, and both the first optical image and the second optical image are obtained by imaging the examinee with visible light from the upper side of the head of the examinee, but the present disclosure is not limited to this. The type and the number of the optical cameras 8 are not particularly limited, and at least one of the first optical image or the second optical image need only be at least one of the visible light image or the depth image. For example, the first optical image may be the visible light image, and the second optical image may be the depth image. In addition, for example, the first optical image may be obtained by imaging the examinee from the upper side of the head, and the second optical image may be obtained by imaging the examinee from the back surface side.

For example, a plurality of images may be used in combination as the first optical image. For example, the visible light image and the depth image may be combined as the first optical image. For example, the visible light image (see FIG. 17) in which the back side of the examinee is included and the depth image in which the back side of the examinee is included may be combined, the X coordinate of the reference position may be specified based on the visible light image, and the Y coordinate of the reference position may be specified based on the depth image.

In addition, in the embodiment described above, the example is described in which the mammography image and the ultrasound image that can be captured by the imaging apparatus 10 are applied as examples of the first medical image and the second medical image, but the present disclosure is not limited to this. As the first medical image and the second medical image, for example, a computed tomography image (CT image), a magnetic resonance image (MRI image), or the like captured by a medical image capturing apparatus other than the imaging apparatus 10 may be applied. Therefore, for example, the first medical image may be the mammography image, and the second medical image may be the computed tomography image. In addition, for example, the first medical image may be the mammography image, and the second medical image may be the magnetic resonance image.

In addition, in the embodiment described above, the form is described in which the console 50 is an example of a control apparatus according to the present disclosure, but an apparatus other than the console 50 may have the function of the control apparatus according to the present disclosure. In other words, an apparatus other than the console 50, such as the imaging apparatus 10 and the external apparatus, may have a part or all of the functions of the acquisition unit 60, the specifying unit 62, and the controller 66. For example, the external apparatus may specify the first reference position based on the first optical image, to store the first reference position in the storage medium in association with the first medical image, and the console 50 may only acquire the first medical image associated with the first reference position from the storage medium.

In the embodiment described above, for example, as hardware structures of processing units that execute various types of processes, such as the controller 20, the acquisition unit 60, the specifying unit 62, and the controller 66, various processors shown below can be used. As described above, in addition to the CPU that is a general-purpose processor that executes software (program) to function as various processing units, the various processors include a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute a specific process, such as an application specific integrated circuit (ASIC).

One processing unit may be configured by using one of the various processors or may be configured by using a combination of two or more processors of the same type or different types (for example, a combination of a plurality of FPGAs or a combination of a CPU and an FPGA). Moreover, a plurality of processing units may be configured of one processor.

A first example of the configuration in which the plurality of processing units are configured by using one processor is a form in which one processor is configured by using a combination of one or more CPUs and the software and this processor functions as the plurality of processing units, as represented by computers, such as a client and a server. Second, as represented by a system on chip (SoC) or the like, there is a form in which the processor is used in which the functions of the entire system which includes the plurality of processing units are realized by a single integrated circuit (IC) chip. In this way, as the hardware structure, the various processing units are configured by using one or more of the various processors described above.

Further, the hardware structure of these various processors is, more specifically, an electric circuit (circuitry) in which circuit elements such as semiconductor elements are combined.

In addition, in the embodiment described above, the aspect is described in which the various programs in the imaging apparatus 10 are stored (installed) in the ROM included in the controller 20 in advance, and the information processing program 57 in the console 50 is stored in the storage unit 52 in advance, but the present disclosure is not limited to this. The various programs and the information processing program 57 in the imaging apparatus 10 may be provided in a form of being recorded in a recording medium, such as a compact disc read only memory (CD-ROM), a digital versatile disc read only memory (DVD-ROM), and a universal serial bus (USB) memory. In addition, a form may be adopted in which the various programs and the information processing program 57 in the imaging apparatus 10 are downloaded from an external apparatus via the network. Further, the technique of the present disclosure extends to a storage medium that non-transitorily stores a program in addition to the program.

In the technique of the present disclosure, the embodiment and the examples described above can be combined as appropriate. The above-described contents and the above-shown contents are detailed description for parts according to the technique of the present disclosure, and are merely examples of the technique of the present disclosure. For example, the above description related to the configuration, the function, the action, and the effect is the description related to the examples of the configuration, the function, the action, and the effect of the parts according to the technique of the present disclosure. As a result, it is needless to say that unnecessary parts may be deleted, new elements may be added, or replacements may be made with respect to the above-described contents and the above-shown contents within a range that does not deviate from the gist of the technique of the present disclosure.

What is claimed is:

1. An information processing apparatus comprising at least one processor, wherein the processor is configured to:

acquire a first medical image of an examinee associated with a first reference position specified based on a physical feature of the examinee included in a first optical image obtained by optically imaging the examinee;

acquire a second medical image of the examinee associated with the first reference position or a second reference position indicating a position substantially the same as the first reference position; and output the first medical image and the second medical image by registering the first medical image with the second medical image based on the first reference position and the second reference position, wherein the first medical image is a mammography image obtained by a mammography apparatus, the first reference position is expressed by coordinate points indicating a plurality of joint points of the examinee included in the first optical image, and the second reference position is expressed by coordinate points indicating a plurality of joint points of the examinee included in a second optical image that is newly obtained.

2. The information processing apparatus according to claim 1, wherein the processor is configured to:

acquire the first optical image;

specify the first reference position based on the physical feature of the examinee included in the first optical image; and associate the first medical image with the specified first reference position.

3. The information processing apparatus according to claim 1, wherein the first optical image and the first medical image are images captured at first points in time that are substantially the same each other.

4. The information processing apparatus according to claim 1, wherein the processor is configured to:

acquire a second optical image obtained by optically imaging the examinee at a second point in time that is substantially the same as an imaging point in time of the second medical image;

specify the second reference position based on a physical feature of the examinee included in the second optical image; and associate the specified second reference position with the second medical image.

5. The information processing apparatus according to claim 1, wherein the processor is configured to store the output in a storage unit.

6. The information processing apparatus according to claim 1, wherein the processor is configured to perform registration between the first medical image and the second medical image based on the first reference position and the second reference position, to display the first medical image and the second medical image on a display or to print the first medical image and the second medical image on paper by using a printer.

7. The information processing apparatus according to claim 1, wherein the first optical image is an image obtained by optically imaging a portion that is not included in the first medical image of the examinee.

8. The information processing apparatus according to claim 7, wherein the physical feature of the examinee is a joint point of the examinee.

9. The information processing apparatus according to claim 7, wherein the first optical image is an image obtained by imaging the examinee from a back surface side of the examinee.

10. The information processing apparatus according to claim 7, wherein the first optical image is an image obtained by imaging the examinee from an upper side of a head of the examinee.

11. The information processing apparatus according to claim 1, wherein the first optical image is at least one of a visible light image or a depth image.

12. The information processing apparatus according to claim 1, wherein:

the second medical image is an ultrasound image.

13. The information processing apparatus according to claim 1, wherein:

the second medical image is a computed tomography image.

14. The information processing apparatus according to claim 1, wherein:

the second medical image is a magnetic resonance image.

15. The information processing apparatus according to claim 1, wherein:

the first medical image is a mammography image of a left breast of the examinee, and the second medical image is a mammography image of a right breast of the examinee.

16. The information processing apparatus according to claim 1, wherein:

the first medical image is a mammography image captured by setting an imaging distance from a focus of a radiation source to a breast as a subject to a first distance, the second medical image is a magnification mammography image captured by setting the imaging distance to a second distance shorter than the first distance, and the processor is configured to:

derive a magnification ratio of the second medical image based on the second distance;

reduce the second medical image based on the magnification ratio; and output a result of associating the reduced second medical image with the first medical image.

17. The information processing apparatus according to claim 1, wherein the coordinate points of the first reference position include an X coordinate that is a center in X direction of two joint points of the examinee included in the first optical image, and a Y coordinate that is a center in Y direction of the two joint points of the examinee.

18. The information processing apparatus according to claim 17, wherein the coordinate points of the first reference position further include a Z coordinate that is a height from a floor surface to an imaging portion of the examinee.

19. An information processing method comprising:

acquiring a first medical image of an examinee associated with a first reference position specified based on a physical feature of the examinee included in a first optical image obtained by optically imaging the examinee;

acquiring a second medical image of the examinee associated with the first reference position or a second reference position indicating a position substantially the same as the first reference position; and outputting the first medical image and the second medical image by registering the first medical image with the second medical image based on the first reference position and the second reference position, wherein the first medical image is a mammography image obtained by a mammography apparatus, the first reference position is expressed by coordinate points indicating a plurality of joint points of the examinee included in the first optical image, and the second reference position is expressed by coordinate points indicating a plurality of joint points of the examinee included in a second optical image that is newly obtained.

20. A non-transitory computer-readable storage medium storing an information processing program for causing a computer to execute a process comprising:

acquiring a first medical image of an examinee associated with a first reference position specified based on a physical feature of the examinee included in a first optical image obtained by optically imaging the examinee;

acquiring a second medical image of the examinee associated with the first reference position or a second reference position indicating a position substantially the same as the first reference position; and outputting the first medical image and the second medical image by registering the first medical image with the second medical image based on the first reference position and the second reference position, wherein the first medical image is a mammography image obtained by a mammography apparatus, the first reference position is expressed by coordinate points indicating a plurality of joint points of the examinee included in the first optical image, and the second reference position is expressed by coordinate points indicating a plurality of joint points of the examinee included in a second optical image that is newly obtained.

* * * * *